US008425897B2

(12) United States Patent
Jooss et al.

(10) Patent No.: US 8,425,897 B2
(45) Date of Patent: Apr. 23, 2013

(54) COMPOSITIONS CONTAINING LAG-3 AND CELLS THAT SECRETE GM-CSF AND METHODS OF USE

(75) Inventors: Karin Jooss, Bellevue, WA (US); Betty Li, San Francisco, CA (US); Frederic Triebel, Versailles (FR)

(73) Assignee: Immutep S.A., Orsay Cedex (FR)

( * ) Notice: Subject to any disclaimer, the term of this patent is extended or adjusted under 35 U.S.C. 154(b) by 331 days.

(21) Appl. No.: 12/201,905

(22) Filed: Aug. 29, 2008

(65) Prior Publication Data

US 2009/0130054 A1   May 21, 2009

Related U.S. Application Data

(60) Provisional application No. 60/967,105, filed on Aug. 30, 2007.

(51) Int. Cl.
*A01N 63/00* (2006.01)
*A61N 48/00* (2006.01)
*C12N 15/00* (2006.01)
*C12N 5/00* (2006.01)

(52) U.S. Cl.
USPC .......................... 424/93.2; 435/325; 514/885

(58) Field of Classification Search ........................ None
See application file for complete search history.

(56) References Cited

U.S. PATENT DOCUMENTS

| | | | |
|---|---|---|---|
| 5,078,996 A | 1/1992 | Conlon, III et al. | |
| 5,098,702 A | 3/1992 | Zimmerman et al. | |
| 5,225,348 A | 7/1993 | Nagata et al. | |
| 5,266,491 A | 11/1993 | Nagata et al. | |
| 5,436,146 A | 7/1995 | Shenk et al. | |
| 5,637,483 A | 6/1997 | Dranoff et al. | |
| 5,665,577 A | 9/1997 | Sodroski et al. | |
| 5,753,500 A | 5/1998 | Shenk et al. | |
| 5,872,005 A | 2/1999 | Wang et al. | |
| 5,904,920 A | 5/1999 | Dranoff et al. | |
| 5,955,331 A | 9/1999 | Danos et al. | |
| 5,981,276 A | 11/1999 | Sodroski et al. | |
| 5,985,290 A | 11/1999 | Jaffee et al. | |
| 6,033,674 A | 3/2000 | Jaffee et al. | |
| 6,037,177 A | 3/2000 | Snyder | |
| 6,040,183 A | 3/2000 | Ferrari et al. | |
| 6,093,570 A | 7/2000 | Ferrari et al. | |
| 6,350,445 B1 | 2/2002 | Jaffee et al. | |
| 6,428,953 B1 | 8/2002 | Naldini et al. | |
| 6,464,973 B1 | 10/2002 | Levitsky et al. | |
| 6,506,604 B2 | 1/2003 | Finer et al. | |
| 2004/0197312 A1 | 10/2004 | Moskalenko et al. | |
| 2006/0110755 A1* | 5/2006 | Duke et al. ........................ 435/6 | |
| 2007/0231298 A1 | 10/2007 | Li et al. | |

FOREIGN PATENT DOCUMENTS

| | | |
|---|---|---|
| WO | WO 92/05262 | 4/1992 |
| WO | WO 98/46728 | 10/1998 |
| WO | WO 99/38954 | 8/1999 |
| WO | WO 00/72686 | 12/2000 |
| WO | WO 2007/126805 A2 | 11/2007 |
| WO | WO 2007/150077 A2 | 12/2007 |

OTHER PUBLICATIONS

Walczak et al., Expert Opin. Investig. Drugs, 2002, 11: 1737-1748.*
PCT International Search Report dated Mar. 27, 2009, in International Application No. PCT/US2008/010335, filed Aug. 29, 2009.
Brignone et al., 2007. "IMP321 (sLAG-3), an Immunopotentiator for T-cell Responses Against a HBsAg Antigen in Healthy Adults: A Single Blind Randomised Controlled Phase I Study," *Journal of Immune Based Therapies and Vaccines*, Biomed Central Ltd., London, GB, vol. 5(5):1-15.
Buisson et al., 2005, "LAG-3 (CD223) Reduces Macrophage and Dendritic Cell Differentiation from Monocyte Precursors," *Immunology*, vol. 114:369-374.
Di Carlo et al., 2005. "Immunological Mechanisms Elicited at the Tumour Site by Lymphocyte Activation Gene-3 (LAG-3) Versus IL-12; Sharing a Common Th1 Anti-Tumour Immune Pathway," *Journal of Pathology*, GB, vol. 205:82-91.
Li et al., 2007, "Established B16 Tumors are Rejected Following Treatment with GM-CSF-Secreting Tumor Cell Immunotherapy in Combination with Anti-4-1BB mAb," *Clinical Immunology*, Academic Press, U.S., vol. 125:76-87.
Li et al. 2007, "Recombinant IL-7 Enhances the Potency of GM-CSF-Secreting Tumor Cell Immunotherapy," *Clinical Immunology*, Academic Press, US, vol. 123:155-165.
Li et al., 2008, "Lymphocyte Activation Gene-3 Fusion Protein Increases the Potency of a Granulocyte Macrophage Colony-Stimulating Factor-Secreting Tumor Cell Immnotherapy," *Clinical Cancer Research*: An Official Journal of the American Association for Cancer Research, vol. 14(11):3545-3554.
Simmons et al., 2007, "GM-CSF-Secreting Cancer Immunotherapies: Preclinical Analysis of the Mechanism of Action," *Cancer Immunology*, Immunotherapy, Springer, Berlin, DE, vol. 56:1653-1665.
Altschul et al., 1990, Basic Local Alignment Search Tool, J. Molecular Biol., vol. 215:403-410.
Altschul et al., 1997, "Gapped BLAST and PSI-BLAST: A New Generation of Protein Database Search Programs," Nucleic Acids Res., vol. 25(17):3389-3402.
Aoki et al., 1992, "Expression of Murine Interleukin 7 in a Murine Glioma Cell Line Results in Reduced Tumorigenicity In Vivo," PNAS, vol. 89:3850-3854.
Armstrong et al., 2002, "Cytokine Modified Tumor Vaccines," Surg. Oncology Clin. N. Am., vol. 11:681-696.
Asher et al., 1991, "Murine Tumor Cells Transduced With the Gene for Tumor Necrosis Factor-α," J. Immunol., vol. 146:3227-3234.
Berkelhammer et al., 1982, "Development of a New Melanoma Model in C57BL/6 Mice," Cancer Research, vol. 42:3157-3163.
Bodey et al., 2000, "Failure of Cancer Vaccines: The Significant Limitations of this Approach to Immunotherapy," Anticancer Research, vol. 20:2665-2676.

(Continued)

*Primary Examiner* — Prema Mertz
(74) *Attorney, Agent, or Firm* — Morrison & Foerster LLP

(57) ABSTRACT

The present invention relates to a method of enhancing anti-tumor protection in a mammal. More particularly, the invention is concerned with combinations comprising antigen presenting cell (APC) activators and a cytokine-secreting cell and methods of administering the combination for enhanced immune response to tumor cells in a patient with a cancer.

6 Claims, 10 Drawing Sheets

OTHER PUBLICATIONS

Brignone et al., 2007, "IMP321 (sLAG-3), an Immunopotentiator for T Cell Responses Against a HBsAg Antigen in Healthy Adults: a Single Blind Randomised Controlled Phase I Study," J. of Immune Based Ther. and Vaccines, vol. 5:1-15.

Cantrell et al., 1985, "Cloning, Sequence, and Expression of a Human Granulocyte/Macrophage Colony-Stimulating Factor," PNAS, vol. 82:6250-6254.

Chang et al., 2000, "Immunogenetic Therapy of Human Melanoma Utilizing Autologous Tumor Cells Transduced to Secrete Granulocyte-Macrophage Colony-Stimulating Factor," Human Gene Therapy, vol. 11:839-850.

Darrow et al., 1989, "The Role of HLA Class I Antigens in Recognition of Melanoma Cells by Tumor-Specific Cytotoxic T Lymphocytes," vol. 142:3329-3335.

Dranoff et al., 1993, "Vaccination with Irradiated Tumor Cells Engineered to Secrete Murine Granulocyte-Macrophage Colony-Stimulating Factor Stimulates Potent, Specific, and Long-Lasting Anti-Tumor Immunity," PNAS, vol. 90:3539-3543.

Dummer et al., 2001, "GVAX Cell Genesys," Current Opinion in Investigational Drugs, vol. 2(6):844-848.

El Mir & Triebel, J. 2000, "A Soluble Lymphocyte Activation Gene-3 Molecule Used as a Vaccine Adjuvant Elicits Greater Humoral and Cellular Immune Responses to Both Particulate and Soluble Antigens," J. Immunol., vol. 164:5583-5589.

Fearon et al., 1990, "Interleukin-2 Production by Tumor Cells Bypasses T Helper Function in the Generation of an Antitumor Response," Cell, vol. 60:397-403.

Gansbacher et al., 1990, "Retroviral Vector-Mediated γ-Interferon Gene Transfer into Tumor Cells Generates Potent and Long Lasting Antitumor Immunity," Cancer Research, vol. 50:7820-7825.

Gansbacher et al., 1990, "Interleukin 2 Gene Transfer into Tumor Cells Abrogates Tumorigenicity and Induces Protective Immunity," J. Exp. Med. vol. 172:1217-1224.

Golumbeck et al., 1991, "Treatment of Established Renal Cancer by Tumor Cells Engineered to Secrete Inerleukin-4," Science, vol. 254:713-716.

Griswold, DP Jr., 1972, "Consideration of the Subcutaneously Implanted B16 Melanoma as a Screening Model for Potential Anticancer Agents," Cancer Chemother. Rep., vol. 2;3(1):315-324.

Guo et al., 1996, "Evaluation of Promoter Strength for Hepatic Gene Expression In Vivo Following Adenovirus-Mediated Gene Transfer," Gene Therapy, vol. 3(9):802-810.

Havell et al., 1988, "The Antitumor Function of Tumor Necrosis Factor (TNF) 1. Therapeutic Action of TNF Against an Established Murine Sarcoma is Indirect, Immunologically Dependent, and Limited by Severe Toxicity," J. Exp. Med., vol. 167:1067-1085.

Simons et al., 1997, "Bioactivity of Autologous Irradiated Renal Cell Carcinoma Vaccines Generated by ex Vivo Granulocyte-Macrophage Colony-Stimulating Factor Gene Transfer," Cancer Research, vol. 57:1537-1546.

Simons et al., 1999, "Induction of Immunity to Prostate Cancer Antigens: Results of a Clinical Trial of Vaccination with Irradiated Autologous Prostate Tumor Cells Engineered to Secrete Granulocyte-Macrophage Colony-Stimulating Factor Using ex vivo Gene Transfer," Cancer Research, vol. 59(20):5160-5168.

Soiffer et al., 1998, "Vaccination with Irradiated Autologous Melanoma Cells Engineered to Secrete Human Granulocyte-Macrophage Ccolony-Stimulating Factor Generates Potent Antitumor Immunity in Patients with Metastatic Melanoma," PNAS, vol. 95:13141-13146.

Triebel et al., 1990, LAG-3, A Novel Lymphocyte Activation Gene Closely Related to CD4, J. Exp. Med., vol. 171:1393-1405.

Triebel et al., 2003, "LAG-3: A Regulator of T-Cell and DC Responses and its Use in Therapeutic Vaccination," Trends in Immunology, vol. 24:619-622.

Ye et al., 1999, "Regulated Delivery of Therapeutic Proteins After in Vivo Somatic Cell Gene Transfer," Science, vol. 283:88-91.

Hock et al., 1991, "Interleukin 7 Induces CD4+ T Cell-Dependent Tumor Rejection," J. Exp. Med., vol. 174:1291-1298.

Hom et al., 191, "Common Expression of Melanoma Tumor-Associated Antigens Recognized by Human Tumor Infiltrating Lymphocytes: Analysis by Human Lymphocyte Antigen Restriction," Journal of Immunotherapy, vol. 10:153-164.

Hu et al., 2002, "Development of Antitumor Immune Responses in Reconstituted Lymphopenic Hosts," Cancer Research, vol. 62:3914-3919.

Huang et al., 1994, "Role of Bone marrow-Derived Cells in Presenting MHC Class I-Restricted Tumor Antigens," Science, vol. 264:961-965.

Huard et al., 1997, "Characterization of the Major Histocompatibility Complex Class II Binding Site on LAG-3 Protein," PNAS, vol. 94:5744-5749.

Huebner et al., 1985, "The Human Gene Encoding GM-CSF is at 5q21-q32, the Chromosome Region Deleted in the 5q- Anomaly," Science, vol. 230(4731):1282-1285.

Ill et al., 1997, "Optimization of the Human Factor VIII Complementary DNA Expression Plasmid for Gene Therapy of Hemophilia A," Blood Coagul Fibrinolysis, 8 Suppl. 2:S23-S30.

Jaffee et al., 2001, "Novel Allogeneic Granulocyte-Macrophage Colony-Stimulalting Factor-Secreting Tumor Vaccine for Pancreatic Cancer: A Phase I Trail of Safety and Immune Activation," Journal of Clinical Oncology, vol. 19(1):145-156.

Jaffee et al., 1995, "Gene Therapy: Its Potential Application in the Treatment of Renal-Cell Carcinoma," Seminars in Oncology, vol. 22:81-91.

Kawakami et al., 1992, "Shared Human Melanoma Antigens, Recognition by Tumor-Infiltrating Lymphocytes in HLA-A2.1-Transfected Melanomas," J. Immunol., vol. 148:638-643.

Kim et al., 1990, "Use of Human Elongation Factor 1α Promoter as a Versatile and Efficient Expression System," Gene, vol. 91(2):217-223.

Klein et al., 1976, "Properties of the K562 Cell Line, Derived From a Patient with Chronic Myeloid Leukemia," Int. J. Cancer, vol. 18:421-431.

Lee et al., 1997, "Genetic Immunotherapy of Established Tumors with Adenovirus-Murine Granulocyte-Macrophage Colony-Stimulating Factor," Human Gene Therapy, vol. 8:187-193.

Nagai et al., 1998, "Irradiated Tumor Cells Adenovirally Engineered to Secrete Granulocyte/Macrophage-Colony-Stimulating Factor Establish Antitumor Immunity and Eliminate Pre-Existing Tumors in Syngeneic Mice," Cancer Immunol Immunother, vol. 47:72-80.

Plaksin et al., 1994, "Effective Anti-Metastatic Melonoma Vaccination with Tumor Cells Transfected with Mice Genes and/or Infected with Newcastle Disease Virus (NDV)," Int. J. Cancer, vol. 59:796-801.

Porgador et al., 1994, "Immunotherapy of Tumor Metastasis via Gene Therapy," Nat. Immun,, vol. 13:113-130.

Prigent et al., 1999, "Lymphocyte Activation Gene-3 Induces Tumor Regression and Antitumor Immune Responses," Euro. J. Immun., vol. 29:3867-3876.

Rivera et al., 1996, "A Humanized System for Pharmacologic Control of Gene Expression," Nature Med., vol. 2(9):1028-1032.

Salgia et al., 2003, "Vaccination with Irradiated Autologous Tumor Cells Engineered to Secrete Granulocyte-Macrophage Colony-Stimulating Factor Augments Antitumor Immunity in Some Patients with Metastatic Non-Small-Cell Lung Carcinoma," J. Clinical Oncol., vol. 624-230.

Salvadori et al., 1995, B7-1 Amplifies the Response to Interleukin-2-Secreting Tumor Vaccines In Vivo, but Fails to Induce a Response by Naïve Cells In Vitro, Human Gene Therapy, vol. 6:1299-1306.

Samulski et al., 1989, "Helper-Free Stocks of Recombinant Adeno-Associated Viruses: Normal Integration Does Not Require Viral Gene Expression," Journal of Virology, vol. 63:3822-3828.

Sawyer et al., 2002, "Src Homology-2 Inhibitors: Peptidomimetic and Nonpeptides," Mini. Rev. in Med. Chem., vol. 2(5):475-488.

* cited by examiner

SEQUENCE LISTING

<160> NUMBER OF SEQ ID NOS: 2

<210> SEQ ID NO 1
<211> LENGTH: 503
<212> TYPE: PRT
<213> ORGANISM: Artificial Sequence
<220> FEATURE:
<223> OTHER INFORMATION: Human LAG-3 Protein

<400> SEQUENCE: 1

```
Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
    290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350
```

```
Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Leu Leu Phe Leu
                420                 425                 430

Thr Leu Gly Val Leu Ser Leu Leu Leu Leu Val Thr Gly Ala Phe Gly
            435                 440                 445

Phe His Leu Trp Arg Arg Gln Trp Arg Pro Arg Arg Phe Ser Ala Leu
        450                 455                 460

Glu Gln Gly Ile His Pro Pro Gln Ala Gln Ser Lys Ile Glu Glu Leu
465                 470                 475                 480

Glu Gln Glu Pro Glu Pro Glu Pro Glu Pro Glu Pro Glu Pro Glu Pro
                485                 490                 495

Glu Pro Glu Pro Glu Gln Leu
            500
```

<210> SEQ ID NO 2
<211> LENGTH: 654
<212> TYPE: PRT
<213> ORGANISM: Artificial Sequence
<220> FEATURE:
<223> OTHER INFORMATION: A soluble form of the LAG-3 Protein (hLAG-3Ig)

<400> SEQUENCE: 2

```
Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
```

```
                    210                 215                 220
Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                    245                 250                 255

Gly Leu Pro Cys Arg Leu Pro Ala Gly Val Gly Thr Arg Ser Phe Leu
                260                 265                 270

Thr Ala Lys Trp Thr Pro Pro Gly Gly Pro Asp Leu Leu Val Thr
            275                 280                 285

Gly Asp Asn Gly Asp Phe Thr Leu Arg Leu Glu Asp Val Ser Gln Ala
290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
                340                 345                 350

Ser Gly Gln Glu Arg Phe Val Trp Ser Ser Leu Asp Thr Pro Ser Gln
            355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Asp Asp Asp
                405                 410                 415

Lys Gly Ser Gly Ser Gly Glu Pro Lys Ser Cys Asp Lys Thr His Thr
                420                 425                 430

Cys Pro Pro Cys Pro Ala Pro Glu Leu Leu Gly Gly Pro Ser Val Phe
            435                 440                 445

Leu Phe Pro Pro Lys Pro Lys Asp Thr Leu Met Ile Ser Arg Thr Pro
            450                 455                 460

Glu Val Thr Cys Val Val Val Asp Val Ser His Glu Asp Pro Glu Val
465                 470                 475                 480

Lys Phe Asn Trp Tyr Val Asp Gly Val Glu Val His Asn Ala Lys Thr
                485                 490                 495

Lys Pro Arg Glu Glu Gln Tyr Asn Ser Thr Tyr Arg Val Val Ser Val
            500                 505                 510

Leu Thr Val Leu His Gln Asp Trp Leu Asn Gly Lys Glu Tyr Lys Cys
            515                 520                 525

Lys Val Ser Asn Lys Ala Leu Pro Ala Pro Ile Glu Lys Thr Ile Ser
530                 535                 540

Lys Ala Lys Gly Gln Pro Arg Glu Pro Gln Val Tyr Thr Leu Pro Pro
545                 550                 555                 560

Ser Arg Asp Glu Leu Thr Lys Asn Gln Val Ser Leu Thr Cys Leu Val
                565                 570                 575

Lys Gly Phe Tyr Pro Ser Asp Ile Ala Val Glu Trp Glu Ser Asn Gly
                580                 585                 590

Gln Pro Glu Asn Asn Tyr Lys Thr Thr Pro Pro Val Leu Asp Ser Asp
            595                 600                 605
```

```
Gly Ser Phe Phe Leu Tyr Ser Lys Leu Thr Val Asp Lys Ser Arg Trp
    610                 615                 620

Gln Gln Gly Asn Val Phe Ser Cys Ser Val Met His Glu Ala Leu His
625                 630                 635                 640

Asn His Tyr Thr Gln Lys Ser Leu Ser Leu Ser Pro Gly Lys
                645                 650
```

COMPOSITIONS CONTAINING LAG-3 AND CELLS THAT SECRETE GM-CSF AND METHODS OF USE

This application claims the benefit of U.S. Provisional Application No. 60/967,105, filed Aug. 30, 2007, the disclosure of which is incorporated herein by reference in its entirety.

FIELD OF THE INVENTION

The present invention relates to a method of enhancing anti-tumor protection in a mammal. More particularly, the invention is concerned with combinations comprising antigen presenting cell (APC) activators and a cytokine-secreting cell and methods of administering the combination for enhanced generation of an immune response to tumor cells in a patient.

BACKGROUND OF THE INVENTION

The immune system plays a critical role in the pathogenesis of a wide variety of cancers. When cancers progress, it is widely believed that the immune system either fails to respond sufficiently or fails to respond appropriately, allowing cancer cells to grow. Currently, standard medical treatments for cancer, including chemotherapy, surgery, radiation therapy and cellular therapy, have clear limitations with regard to both efficacy and toxicity. To date, these approaches have met with varying degrees of success dependent upon the type of cancer, general health of the patient, stage of disease at the time of diagnosis, etc. Improved strategies that combine specific manipulation of the immune response to cancer in combination with standard medical treatments may provide a means for enhanced efficacy and decreased toxicity.

The use of autologous cancer cells as immunotherapies to augment anti-tumor immunity has been explored for some time (Oettgen et al., "The History of Cancer Immunotherapy", In: Biologic Therapy of Cancer, Devita et al. (eds.) J. Lippincot Co., pp 87-199, 1991). However, due to the weak immunogenicity of many cancers, down regulation of MHC molecules, the lack of adequate costimulatory molecule expression and secretion of immunoinhibitory cytokines by cancer cells, the response to such immunotherapies has not resulted in long term efficacy. See, e.g., Armstrong TD and Jaffee E M, Surg Oncol Clin N Am. 11(3):681-96, 2002 and Bodey B et al, Anticancer Res 20(4):2665-76, 2000.

Numerous cytokines have been shown to play a role in regulation of the immune response to tumors. For example, U.S. Pat. No. 5,098,702 describes using combinations of TNF, IL-2 and IFN-beta in synergistically effective amounts to combat existing tumors. U.S. Pat. Nos. 5,078,996, 5,637, 483 and 5,904,920 describe the use of GM-CSF for treatment of tumors. However, direct administration of cytokines for cancer therapy may not be practical, as they are often systemically toxic. (See, for example, Asher et al., J. Immunol. 146: 3227-3234, 1991 and Havell et al, J. Exp. Med. 167: 1067-1085, 1988.)

An expansion of this approach involves the use of genetically modified tumor cells which express cytokines locally at the immunotherapy site. Activity has been demonstrated in tumor models using a variety of immunomodulatory cytokines, including IL-4, IL-2, TNF-alpha, G-CSF, IL-7, IL-6 and GM-CSF, as described in Golumbeck P T et al., Science 254:13-716, 1991; Gansbacher B et al, J. Exp. Med. 172: 1217-1224, 1990; Fearon E R et al., Cell 60:397-403, 1990; Gansbacher B et al., Cancer Res. 50:7820-25, 1990; Teng M et al, PNAS 88:3535-3539, 1991; Columbo M P et al, J. Exp. Med. 174:1291-1298, 1991; Aoki et al., Proc Natl Acad Sci USA. 89(9):3850-4, 1992; Porgador A, et al., Nat Immun. 13(2-3):113-30, 1994; Dranoff G et al., PNAS 90:3539-3543, 1993; Lee C T et al, Human Gene Therapy 8:187-193, 1997; Nagai E et al, Cancer Immunol. Immonther. 47:2-80, 1998 and Chang A et al., Human Gene Therapy 11:839-850, 2000, respectively.

Clinical trials employing GM-CSF-expressing autologous or allogeneic cellular immunotherapies have commenced for treatment of prostate cancer, melanoma, lung cancer, pancreatic cancer, renal cancer, and multiple myeloma (Dummer R., Curr Opin Investig Drugs 2(6):844-8, 2001; Simons J et al, Cancer Res. 15; 59(20):5160-8, 1999; Soiffer R et al., PNAS 95:13141-13146, 1998; Simons J et al., Cancer Res. 15; 57:1537-1546, 1997; Jaffee E et al, J. Clin Oncol. 19:145-156, 2001; and Salgia R et al, J. Clin Oncol. 21:624-630, 2003).

In yet another approach, autologous tumor cells were genetically altered to produce a costimulatory molecule, such as B7-1 or allogeneic histocompatibility antigens (Salvadori et al. Hum. Gene Ther. 6:1299-1306, 1995 and Plaksin et al. Int. J. Cancer 59:796-801, 1994). While the use of genetically modified tumor cells has met with success in treatment of some forms of cancer, there remains a need for improved treatment regimens with greater potency and/or efficacy and fewer side effects than the therapies currently in use.

SUMMARY OF THE INVENTION

The invention provides improved compositions and methods for the treatment of cancer in a mammal, typically a human, by administering a combination of a cytokine-expressing cellular immunotherapy and at least one antigen presenting cell (APC) activator.

In one aspect of the invention, the cytokine-expressing cellular immunotherapy expresses GM-CSF.

In another aspect of the invention, the cytokine-expressing cellular immunotherapy is rendered proliferation-incompetent by irradiation.

In yet a further aspect of the invention, administration of the combination results in enhanced therapeutic efficacy relative to administration of the cytokine-expressing cellular immunotherapy or at least one APC activator alone.

In yet another aspect of the invention, the cytokine-expressing cellular immunotherapy is typically administered subcutaneously, intratumorally, or intradermally. The injection of irradiated GM-CSF-expressing tumor cells results in a local reaction characterized by the infiltration of dendritic cells (DCs), macrophages, and granulocytes.

In one aspect of the invention, at least one APC activator is LAG-3.

In yet another aspect of the invention, the LAG-3 can be administered subcutaneously, intratumorally, intradermally, or intraperitoneally.

In another aspect of the invention, LAG-3 may be administered prior to, at the same time as, or following administration of the cytokine-expressing cellular immunotherapy component of the combination.

The invention further provides a combination of cytokine-expressing cells and an APC activator such as LAG-3, wherein the combination comprises cells that are autologous, allogeneic, or bystander cells.

In another aspect of the invention, the autologous, allogeneic, or bystander cell is rendered proliferation-incompetent by irradiation.

The invention further provides compositions and kits comprising cytokine-expressing cellular immunotherapy combinations for use according to the description provided herein.

BRIEF DESCRIPTION OF THE DRAWINGS

FIGS. 7A and B demonstrate that LAG-3 enhances antigen-specific IgG1 production and has no effect on antigen-specific IgG2 production.

DETAILED DESCRIPTION OF THE INVENTION

Figure 1A:
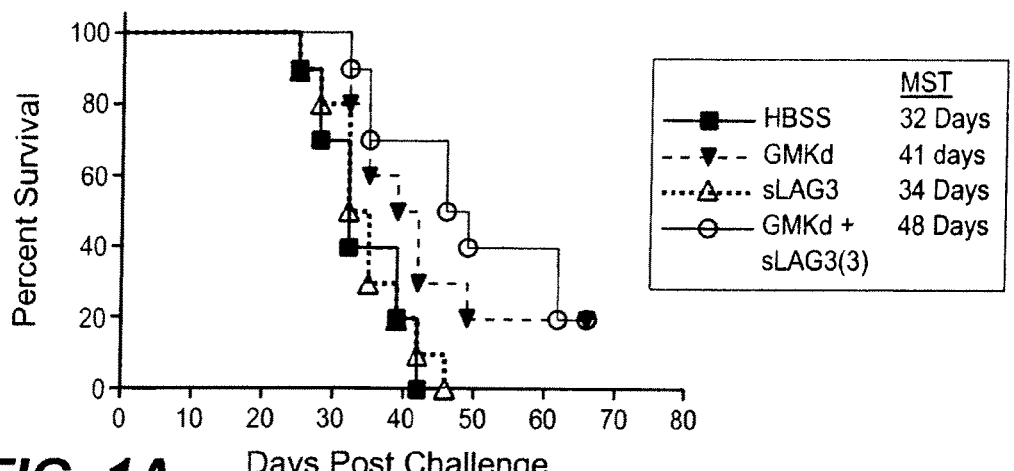
FIG. 1A illustrates the results of treatment with the combination of GM-CSF-secreting tumor cell immunotherapy and LAG-3. On day 0, C57B6 mice were challenged with $2 \times 10^5$ B16F10 tumor cells. 0.1 μg of LAG-3 was premixed with $1 \times 10^6$ irradiated GM-CSF-secreting tumor cell immunotherapy and administered together as subcutaneous injections. Mice were then monitored for the development of subcutaneous tumors twice a week and euthanized when the tumor burden becomes excessive. Mean survival time (MST) of each treatment group is provided.
Figure 1B:
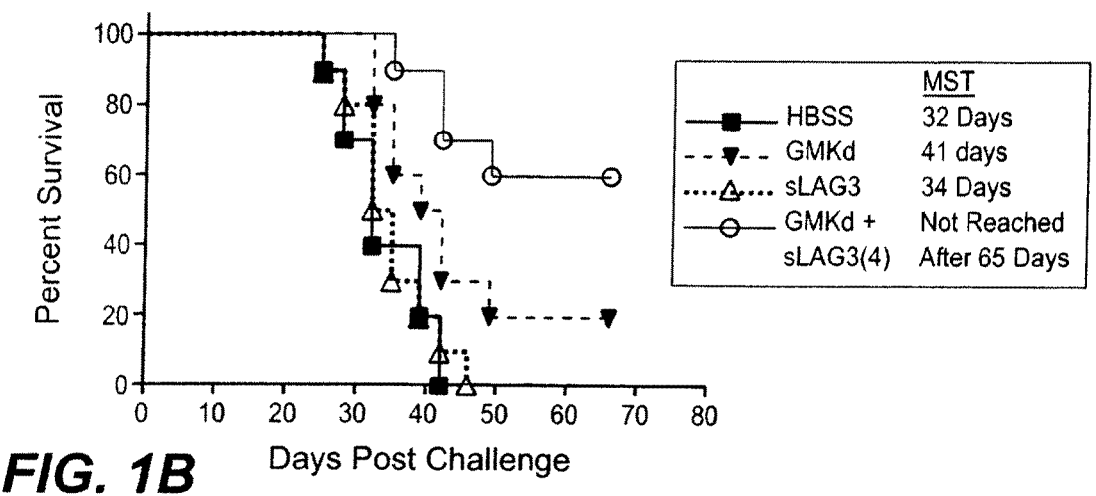
FIG. 1B illustrates the results of treatment with the combination of GM-CSF-secreting tumor cell immunotherapy and LAG-3. On day 0, C57B6 mice were challenged with $2 \times 10^5$ B16F10 tumor cells. 0.1 μg of LAG-3 was administered as subcutaneous injections at the immunotherapy site at day 1 post immunotherapy. Mice were then monitored for the development of subcutaneous tumors twice a week and euthanized when the tumor burden becomes excessive. Mean survival time (MST) of each treatment group is provided, except for mice treated with combination therapy, where 60% of treated mice survived past the end of the study.
Figure 1C:
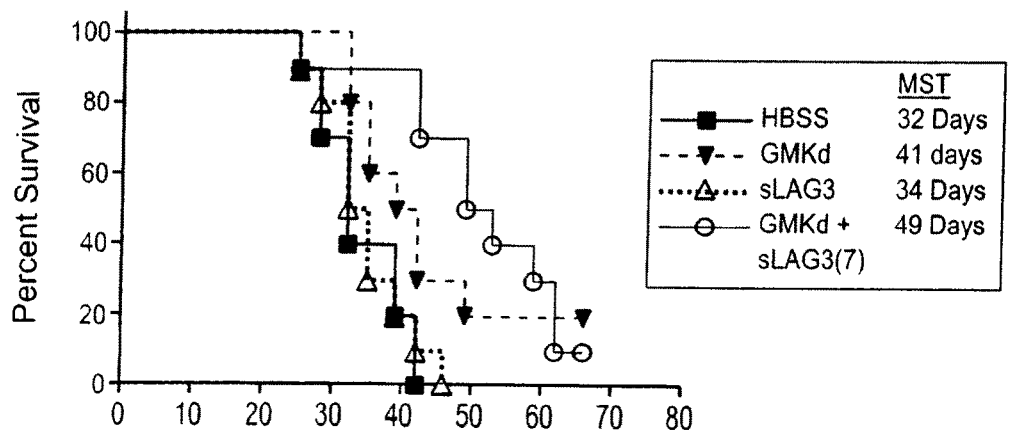
FIG. 1C illustrates the results of treatment with the combination of GM-CSF-secreting tumor cell immunotherapy and LAG-3. On day 0, C57B6 mice were challenged with $2 \times 10^5$ B16F10 tumor cells. 0.1 μg of LAG-3 was administered as subcutaneous injections at the immunotherapy site at day 4 post immunotherapy. Mice were then monitored for the development of subcutaneous tumors twice a week and euthanized when the tumor burden becomes excessive. Mean survival time (MST) of each treatment group is provided.
Figure 1D:
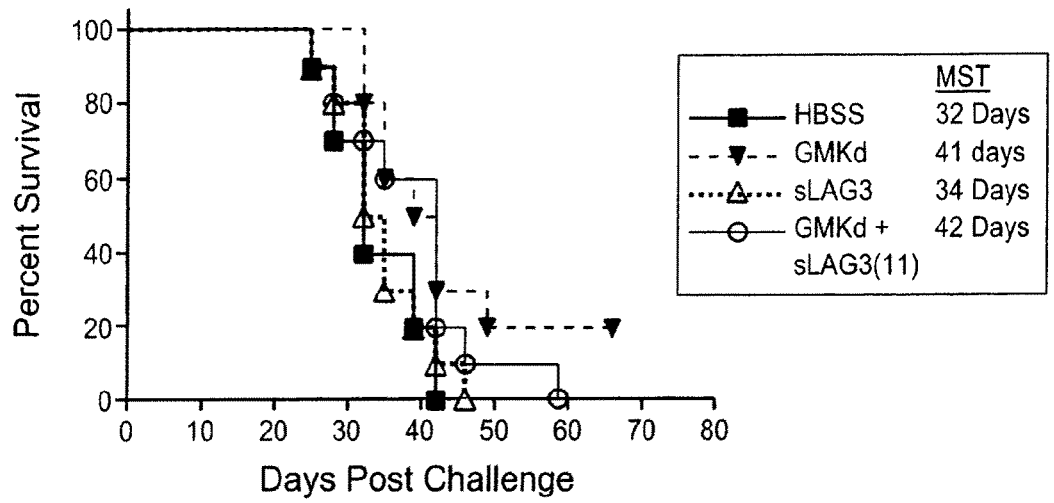
FIG. 1D illustrates the results of treatment with the combination of GM-CSF-secreting tumor cell immunotherapy and LAG-3. On day 0, C57B6 mice were challenged with $2 \times 10^5$ B16F 10 tumor cells. 0.1 μg of LAG-3 was administered as subcutaneous injections at the immunotherapy site at day 7. Mice were then monitored for the development of subcutaneous tumors twice a week and euthanized when the tumor burden becomes excessive. Mean survival time (MST) of each treatment group is provided.

The present invention represents improved cellular immunotherapies for the treatment of cancer in that the compositions and methods described herein comprise at least two components that act in concert to effect an improved therapeutic outcome for the cancer patient under treatment.

The invention is not limited to the specific compositions and methodology described herein. It is also to be understood that the terminology used herein is for the purpose of describing particular embodiments only, and is not intended to limit the scope of the present invention.

Definitions

The terms "regulating the immune response" or "modulating the immune response" as used herein refers to any alteration in a cell of the immune system or any alteration in the activity of a cell involved in the immune response. Such regulation or modulation includes an increase or decrease in the number of various cell types, an increase or decrease in the activity of these cells, or any other changes which can occur within the immune system. Cells involved in the immune response include, but are not limited to, T lymphocytes, B lymphocytes, natural killer (NK) cells, macrophages, eosinophils, mast cells, dendritic cells and neutrophils. In some cases, "regulating" or "modulating" the immune response means the immune response is stimulated or enhanced and in other cases "regulating" or "modulating" the immune response means suppression of the immune system. Stimulation of the immune system may include memory responses and/or future protection against subsequent antigen challenge.

The terms "antigen presenting cell activator", "APC activator or treatment" and the like as used herein refer to antigen presenting cell activator molecule or treatment that stimulates an anti-cancer response when used in combination with a cytokine-expressing cellular immunotherapy. In one aspect, the additional antigen presenting cell activator is expressed by a recombinant tumor cell and may be an immunomodulatory molecule, e.g. a second cytokine. In another aspect, the additional antigen presenting cell activator is administered in the form of a protein or other chemical entity, e.g., an antibody, provided in a pharmaceutically acceptable excipient. In yet another aspect, the antigen presenting cell activator is a standard treatment traditionally used in the treatment of cancer, e.g., radiation. In a further aspect, the additional antigen presenting cell activator is an agent or treatment, which is typically not considered in the treatment of cancer, but which when administered to a patient in combination with a cytokine-expressing cellular immunotherapy results in an improved therapeutic outcome for the patient under treatment.

The term "cytokine" or "cytokines" as used herein refers to the general class of biological molecules which effect/affect cells of the immune system. The definition is meant to include, but is not limited to, those biological molecules that act locally or may circulate in the blood, and which, when used in the compositions or methods of the present invention serve to regulate or modulate an individual's immune response to cancer. Exemplary cytokines for use in practicing the invention include but are not limited to IFN-alpha, IFN-beta, and IFN-gamma, interleukins (e.g., IL-1 to IL-29, in particular, IL-2, IL-7, IL-12, IL-15 and IL-18), tumor necrosis factors (e.g., TNF-alpha and TNF-beta), erythropoietin (EPO), MIP3a, ICAM, macrophage colony stimulating factor (M-CSF), granulocyte colony stimulating factor (G-CSF) and granulocyte-macrophage colony stimulating factor (GM-CSF).

The term "cytokine-expressing cellular immunotherapy" as used herein refers to a composition comprising a population of cells that has been genetically modified to express a cytokine, e.g., GM-CSF, and that is administered to a patient as part of a cancer treatment regimen. The cells of such a "cytokine-expressing cellular immunotherapy" comprise a cytokine-encoding DNA sequence operably linked to expression and control elements such that the cytokine is expressed by the cells. The cells of the "cytokine-expressing cellular immunotherapy" are typically tumor cells and may be autologous or allogeneic to the patient undergoing treatment and or may be "bystander cells" that are mixed with tumor cells taken from the patient. A GM-CSF-expressing "cytokine-expressing cellular immunotherapy" may be referred to herein as "GVAX®".

The term "operably linked" as used herein relative to a recombinant DNA construct or vector means nucleotide components of the recombinant DNA construct or vector are directly linked to one another for operative control of a selected coding sequence. Generally, "operably linked" DNA sequences are contiguous, and, in the case of a secretory leader, contiguous and in reading frame; however, some sequences, e.g., enhancers do not have to be contiguous to be operative and therefore "operably linked."

As used herein, the term "gene" or "coding sequence" means the nucleic acid sequence which is transcribed (DNA) and translated (mRNA) into a polypeptide in vitro or in vivo when operably linked to appropriate regulatory sequences. A "gene" typically comprises the coding sequence plus any non-coding sequences associated with the gene (e.g., regulatory sequences) and hence may or may not include regions preceding and following the coding region, e.g., 5' untranslated (5' UTR) or "leader" sequences and 3' UTR or "trailer" sequences, as well as intervening sequences (introns) between individual coding segments (exons). In contrast, a "coding sequence" does not include non-coding DNA.

The terms "gene-modified" and "genetically-modified" are used herein with reference to a cell or population of cells wherein a nucleic acid sequence has been introduced into the cell or population of cells. The nucleic acid sequence may be heterologous to the cell(s), or it may be an additional copy or altered version of a nucleic acid sequence already present in the cell(s). This term also encompasses cells or a population of cells with altered, e.g., increased or decreased, expression of a nucleic acid sequence endogenous to the cell or population of cells. The cell(s) may be genetically-modified by physical or chemical methods or by the use of recombinant viruses. Chemical and physical methods such as calcium phosphate, electroporation and pressure mediated transfer of genetic material into cells are often used. Several recombinant viral vectors which find utility in effective delivery of genes into mammalian cells include, for example, retroviral vectors, adenovirus vectors, adenovirus-associated vectors (AAV), herpes virus vectors, pox virus vectors. In addition, non-viral means of introduction, for example, naked DNA delivered via liposomes, receptor-mediated delivery, calcium phosphate transfection, electroporation, particle bombardment (gene gun), or pressure-mediated delivery may also be employed to introduce a nucleic acid sequence into a cell or population of cells to render them "gene-modified" or "genetically-modified.

As used herein, the terms "tumor" and "cancer" refer to a cell that exhibits a loss of growth control and forms unusually large numbers of clones of cells. Tumor or cancer cells generally have lost contact inhibition and may be invasive and/or have the ability to metastasize.

The term "antigen from a tumor cell" and "tumor antigen" and "tumor cell antigen" may be used interchangeably herein and refer to any protein, carbohydrate or other component derived from or expressed by a tumor cell which is capable of eliciting an immune response. The definition is meant to include, but is not limited to, whole tumor cells that express some or all of the tumor-associated antigens, tumor cell fragments, plasma membranes taken from a tumor cell, proteins purified from the cell surface or membrane of a tumor cell, or unique carbohydrate moieties associated with the cell surface of a tumor cell. The definition also includes those antigens from the surface of the cell which require special treatment of the cells to access.

The term "systemic immune response" as used herein means an immune response which is not localized, but affects the individual as a whole.

The term "gene therapy" as used herein means the treatment or prevention of cancer by means of ex vivo or in vivo delivery, through viral or non-viral vectors, of compositions containing a recombinant genetic material.

The term "ex vivo" delivery as used herein means the introduction, outside of the body of a human, of compositions containing a genetic material into a cell, tissue, organoid, organ, or the like, followed by the administration of cell, tissue, organoid, organ, or the like which contains such introduced compositions into the body of the same (autologous) or a different (allogeneic) human, without limitation as to the formulation, site or route of administration.

The terms "inactivated cells", "non-dividing cells" and "non-replicating cells" may be used interchangeably herein and refer to cells that have been treated rendering them proliferation incompetent, e.g., by irradiation. Such treatment results in cells that are unable to undergo mitosis, but retain the capability to express proteins such as cytokines or other cancer therapeutic agents. Typically a minimum dose of about 3500 rads is sufficient, although doses up to about 30,000 rads are acceptable. Effective doses include, but are not limited to, 5000 to 10000 rads. Numerous methods of inactivating cells, such as treatment with Mitomycin C, are known in the art. Any method of inactivation which renders cells incapable of cell division, but allows the cells to retain the ability to express proteins may be used in accordance with the present invention.

As used herein "treatment" of an individual or a cell is any type of intervention used in an attempt to alter the natural course of the individual or cell. Treatment includes, but is not limited to, administration of e.g., a cytokine-expressing cellular immunotherapy and at least one additional cancer therapeutic agent or treatment, and may be performed either prophylactically or subsequent to diagnosis as part of a primary or follow-up therapeutic regimen.

The term "administering" as used herein refers to the physical introduction of a composition comprising a cytokine-expressing cellular immunotherapy and at least one additional cancer therapeutic agent or treatment to a patient with cancer. Any and all methods of introduction are contemplated according to the invention; the method is not dependent on any particular means of introduction. Means of introduction are well-known to those skilled in the art, examples of which are provided herein.

The term "co-administering" as used herein means a process whereby the combination of a cytokine-expressing cellular immunotherapy and at least one additional cancer therapeutic agent or treatment is administered to the same patient. The cytokine-expressing cellular immunotherapy and additional cancer therapeutic may be administered simultaneously, at essentially the same time, or sequentially. If administration takes place sequentially, the cytokine-expressing cellular immunotherapy may be administered before or after a given additional cancer therapeutic agent or treatment. The cytokine-expressing cellular immunotherapy and additional cancer therapeutic agent or treatment need not be administered by means of the same vehicle, the cellular immunotherapy and the additional agent or treatment may be administered one or more times and the number of administrations of each component of the combination may be the same or different. In addition, the cytokine-expressing cellular immunotherapy and additional cancer therapeutic agent or treatment need not be administered at the same site.

The term "therapeutically effective amount" or "therapeutically effective combination" as used herein refers to an amount or dose of a cytokine-expressing cellular immunotherapy together with the amount or dose of an additional agent or treatment that is sufficient to modulate, either by stimulation or suppression, the systemic immune response of an individual. The amount of cytokine-expressing cellular immunotherapy in a given therapeutically effective combination may be different for different individuals, different tumor types and will be dependent upon the one or more additional agents or treatments included in the combination. The "therapeutically effective amount" is determined using procedures routinely employed by those of skill in the art such that an "improved therapeutic outcome" results.

As used herein, the terms "improved therapeutic outcome" and "enhanced therapeutic efficacy", relative to cancer refers to any of a slowing or diminution of the growth of cancer cells or a solid tumor, or a reduction in the total number of cancer cells or total tumor burden. An "improved therapeutic outcome" or "enhanced therapeutic efficacy" therefore means there is an improvement in the condition of the patient according to any clinically acceptable criteria, including, for example, an increase in time to tumor progression, an increase in life expectancy, or an improvement in quality of life.

The term "reversal of an established tumor" as used herein means the suppression, regression, partial or complete disappearance of a pre-existing tumor. The definition is meant to include any diminution, for example, in the size, growth rate, appearance or cellular compositions of a preexisting tumor.

The terms "individual", "subject" as referred to herein is a vertebrate, preferably a mammal, and typically refers to a human.

"LAG-3 protein", "LAG-3", a "LAG3 protein", "LAG3", "sLAG-3," an "sLAG-3 protein", "sLAG3" and an "sLAG3 protein","," may be used interchangeably herein and each refers to LAG-3 protein (CD223) having the sequence of SEQ ID NO.: 1, or a fragment, derivative, or homolog thereof, that is capable of activating an antigen presenting cell (APC). A LAG-3 protein or derivative, fragment, or homolog thereof that is capable of activating an APC can be identified by one skilled in the art using the assay provided in Example 2, below.

A LAG-3 "fragment" as used herein refers to a polypeptide that comprises at least a portion of the LAG-3 polypeptide sequence defined by SEQ ID NO.:1 that is capable of activating an APC. One exemplary fragment of LAG-3 that has such activity is a fragment comprising at least the first two immunoglobulin type extracellular domains of the LAG-3 protein corresponding to amino acid 1 to 159 and 160 to 239 of SEQ ID NO.:1. Another that has such activity is the fragment comprising the four immunoglobulin type extracellular domains of the LAG-3 protein corresponding to amino acids 1 to 412 of the sequence ID No1.

A LAG-3 "derivative," as used herein, refers to a molecule or combination of molecules that comprises at least a portion of the LAG-3 polypeptide sequence defined by SEQ ID NO.: 1, wherein the molecule or combination of molecules is capable of activating an APC. Exemplary LAG-3 derivatives include, for example, a fusion protein comprising a LAG-3 polypeptide sequence, or a portion thereof, and an additional polypeptide sequence at its N-terminal or C-terminal end. Such fusion proteins can be used, for example, to modify physicochemical features of the extracytoplasmic domain of the LAG-3 protein. One exemplary fusion protein comprises a LAG-3 polypeptide sequence, or a portion thereof, and the heavy chain —CH2-CH3 junction region of a human immunoglobulin, such as, e.g., an IgG4 or IgG1 immunoglobulin.

A LAG-3 "homolog," as used herein, refers to a polypeptide that comprises the LAG-3 polypeptide sequence, or a portion thereof, with one or more conservative or nonconservative amino acid substitutions, wherein the homolog is capable of activating an APC. Preferably, the amino acid substitutions of the LAG-3 homolog are conservative substitutions. For some exemplary homologs, the amino acid sequence of the LAG-3 homolog can be about 70%, about 75%, about 80%, about 85%, about 90%, about 91%, about 92%, about 93%, about 94%, about 95%, about 96%, about 97%, about 98%, about 99%, or about 99.5% identical to the LAG-3 polypeptide sequence defined by SEQ ID NO.:1, or a portion thereof. For other exemplary homologs, a nucleic acid encoding the homolog will hybridize to a nucleic acid encoding a LAG-3 polypeptide having the amino acid sequence defined by SEQ ID NO.: 1 under hybridization conditions, e.g., stringent hybridization conditions, low stringency hybridization conditions, medium stringency hybridization conditions, or highly stringent hybridization conditions.

"Conservative substitution" refers to the substitution in a polypeptide of an amino acid with a functionally similar amino acid. The following six groups each contain amino acids that are conservative substitutions for one another:

Alanine (A), Serine (S), and Threonine (T)
Aspartic acid (D) and Glutamic acid (E)
Asparagine (N) and Glutamine (Q)
Arginine (R) and Lysine (K)
Isoleucine (I), Leucine (L), Methionine (M), and Valine (V)
Phenylalanine (F), Tyrosine (Y), and Tryptophan (W).

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids can be found in Tijssen, 1993, *Laboratory Techniques in Biochemistry and Molecular Biology—Hybridization with Nucleic Acid Probes*, part I, chapter 2, "Overview of principles of hybridization and the strategy of nucleic acid probe assays", Elsevier, NY; Sambrook et al, 2001, *Molecular Cloning: A Laboratory Manual*, Cold Spring Harbor Laboratory, 3$^{rd}$ ed., NY; and Ausubel et al., eds., Current Edition, *Current Protocols in Molecular Biology*, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

One example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher)

than that observed for an unrelated probe in the particular hybridization assay indicates detection of a specific hybridization.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.*, 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

Another alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 48 minutes to 72 minutes.

General Techniques

The practice of the present invention can employ, unless otherwise indicated, conventional techniques of molecular biology, microbiology, cell biology, biochemistry and immunology, which are within the knowledge of those of skill of the art. Such techniques are explained fully in the literature, such as, "Molecular Cloning: A Laboratory Manual", third edition (Sambrook et al., 2002); "Current Protocols in Molecular Biology" (F. M. Ausubel et al., eds., 2007); "Culture of Animal Cells: A Manual of Basic Techniqaue," $4^{th}$ edition (R. I. Freshney, ed., 2000), each of which is hereby expressly incorporated herein by reference.

Cancer Targets

The methods and compositions of the invention provide an improved therapeutic approach to the treatment of cancer by co-administration of a cytokine-expressing cellular immunotherapy and at least one antigen presenting cell (APC) or treatment to a patient with cancer. "Cancer" as used herein includes cancer localized in tumors, as well as cancer not localized in tumors, such as, for instance, cancer cells that expand from a local tumor by invasion (i.e., metastasis). The invention finds utility in the treatment of any form of cancer, including, but not limited to, cancer of the bladder, breast, colon, kidney, liver, lung, ovary, cervix, pancreas, rectum, prostate, stomach, epidermis; a hematopoietic tumor of lymphoid or myeloid lineage; a tumor of mesenchymal origin such as a fibrosarcoma or rhabdomyosarcoma; other tumor types such as melanoma, teratocarci-noma, neuroblastoma, glioma, adenocarcinoma and non-small lung cell carcinoma.

Introduction of Cytokine and Antigen Presenting Cell Activator into Cells

In one aspect of the invention, a nucleic acid sequence (i.e., a recombinant DNA construct or vector) encoding a cytokine operably linked to a first promoter, alone or in combination with a nucleic acid sequence encoding antigen presenting cell (APC) activator operably linked to a second promoter is introduced into a cell or population of cells. Any and all methods of introduction into a cell or population of cells, typically tumor cells, are contemplated according to the invention, the method is not dependent on any particular means of introduction and is not to be so construed. The cytokine-encoding nucleic acid sequence may be introduced into the same or a different population of cells as the APC activator-encoding nucleic acid sequence.

The "vector" may be a DNA molecule such as a plasmid, virus or other vehicle, which contains one or more heterologous or recombinant DNA sequences, e.g., a nucleic acid sequence encoding a cytokine or additional antigen presenting cell (APC) activator under the control of a functional promoter and in some cases further including an enhancer that is capable of functioning as a vector, as understood by those of ordinary skill in the art. An appropriate viral vector includes, but is not limited to, a retrovirus, a lentivirus, an adenovirus (AV), an adeno-associated virus (AAV), a simian virus 40 (SV-40), a bovine papilloma virus, an Epstein-Barr virus, a herpes virus, a vaccinia virus, a Moloney murine leukemia virus, a Harvey murine sarcoma virus, a murine mammary tumor virus, and a Rous sarcoma virus. Non-viral vectors are also included within the scope of the invention.

Any suitable vector can be employed that is appropriate for introduction of nucleic acids into eukaryotic tumor cells, or more particularly animal tumor cells, such as mammalian, e.g., human, tumor cells. Preferably the vector is compatible with the tumor cell, e.g., is capable of imparting expression of the coding sequence for a cytokine or antigen presenting cell (APC) activator, and is stably maintained or relatively stably maintained in the tumor cell. Desirably the vector comprises an origin of replication and the vector may or may not also comprise a "marker" or "selectable marker" function by which the vector can be identified and selected. While any selectable marker can be used, selectable markers for use in such expression vectors are generally known in the art and the choice of the proper selectable marker will depend on the host cell. Examples of selectable marker genes which encode proteins that confer resistance to antibiotics or other toxins include ampicillin, methotrexate, tetracycline, neomycin (Southern and Berg, J., 1982), myco-phenolic acid (Mulligan and Berg, 1980), puromycin, zeo-mycin, hygromycin (Sugden et al., 1985) or G418.

In practicing the methods of the present invention, a vector comprising a nucleic acid sequence encoding a cytokine or antigen presenting cell (APC) activator may be transferred to a cell in vitro, preferably a tumor cell, using any of a number of methods which include but are not limited to electroporation, membrane fusion with liposomes, Lipofectamine treatment, high velocity bombardment with DNA-coated microprojectiles, incubation with calcium phosphate-DNA precipitate, DEAE-dextran mediated transfection, infection with modified viral nucleic acids, direct microinjection into single cells, etc. Procedures for the cloning and expression of modified forms of a native protein using recombinant DNA technology are generally known in the art, as described in Ausubel, et al., 2007 and Sambrook, et al., 2002, expressly incorporated by reference, herein.

Reference to a vector or other DNA sequences as "recombinant" merely acknowledges the operable linkage of DNA sequences which are not typically operably linked as isolated from or found in nature. A "promoter" is a DNA sequence that directs the binding of RNA polymerase and thereby promotes RNA synthesis. "Enhancers" are cis-acting elements that stimulate or inhibit transcription of adjacent genes. An enhancer that inhibits transcription also is termed a "silencer". Enhancers can function (i.e. be operably linked to a coding sequence) in either orientation, over distances of up to several kilobase pairs (kb) from the coding sequence and from a position downstream of a transcribed region. Regulatory (expression/control) sequences are operatively linked to a nucleic acid coding sequence when the expression/control sequences regulate the transcription and, as appropriate, translation of the nucleic acid sequence. Thus, expression/control sequences can include promoters, enhancers, transcription terminators, a start codon (i.e., ATG) in front of the coding sequence, a splicing signal for introns, and stop codons.

Recombinant vectors for the production of cellular immunotherapies of the invention provide the proper transcription, translation and processing signals (e.g., splicing and polyadenylation signals) such that the coding sequence for the cytokine or antigen presenting cell (APC) activator is appropriately transcribed and translated in the tumor cells into which the vector is introduced. The manipulation of such signals to ensure appropriate expression in host cells is within the skill of the ordinary skilled artisan. The coding sequence for the cytokine and antigen presenting cell (APC) activator may be under control of (i.e., operably linked to) its own native promoter, or a non-native (e.g. heterologous) promoter, including a constitutive promoter, e.g., the cytomegalovirus (CMV) immediate early promoter/enhancer, the Rous sarcoma virus long terminal repeat (RSV-LTR) or the SV-40 promoter.

Alternately, a tissue-specific promoter (a promoter that is preferentially activated in a particular type of tissue and results in expression of a gene product in that tissue) can be used in the vector. Such promoters include but are not limited to a liver specific promoter (Ill CR, et al., Blood Coagul Fibrinolysis 8 Suppl 2:S23-30, 1997) and the EF-1 alpha promoter (Kim D W et al. Gene. 91(2):217-23, 1990, Guo Z S et al. Gene Ther. 3(9):802-10, 1996; U.S. Pat. Nos. 5,266, 491 and 5,225,348, each of which expressly incorporated by reference herein). Inducible promoters also find utility in practicing the methods described herein, such as a promoter containing the tet responsive element (TRE) in the tet-on or tet-off system as described (ClonTech and BASF), the metallothienein promoter which can be upregulated by addition of certain metal salts and rapamycin inducible promoters (Rivera et al., 1996, Nature Med, 2(9): 1028-1032; Ye et al., 2000, Science 283: 88-91; Sawyer T K et al., 2002, Mini Rev Med Chem. 2(5):475-88). Large numbers of suitable tissue-specific or regulatable vectors and promoters for use in practicing the current invention are known to those of skill in the art and many are commercially available.

Exemplary vector systems for use in practicing the invention include the retroviral MFG vector, described in U.S. Pat. No. 5,637,483, expressly incorporated by reference herein. Other useful retroviral vectors include pLJ, pEm and [alpha] SGC, described in U.S. Pat. No. 5,637,483 (in particular Example 12), U.S. Pat. Nos. 6,506,604, 5,955,331 and U.S. Ser. No. 09/612,808, each of which is expressly incorporated by reference herein.

Further exemplary vector systems for use in practicing the invention include second, third and fourth generation lentiviral vectors, U.S. Pat. Nos. 6,428,953, 5,665,577 and 5,981, 276 and WO 00/72686, each of which is expressly incorporated by reference herein.

Additional exemplary vector systems for use in practicing the present invention include adenoviral vectors, described for example in U.S. Pat. No. 5,872,005 and International Patent Publication No. WO 00/72686, each of which is expressly incorporated by reference herein.

Yet another vector system that is preferred in practicing the methods described herein is a recombinant adeno-associated vector (rAAV) system, described for example in International Patent Publication Nos. WO 98/46728 and WO 00/72686, Samulski et al., Virol. 63:3822-3828 (1989) and U.S. Pat. Nos. 5,436,146, 5,753,500, 6,037,177, 6,040,183 and 6,093, 570, each of which is expressly incorporated by reference herein.

Cytokines

Cytokines and combinations of cytokines have been shown to play an important role in the stimulation of the immune system. The term "cytokine" is understood by those of skill in the art, as referring to any immunopotentiating protein (including a modified protein such as a glycoprotein) that enhances or modifies the immune response to a tumor present in the host. The cytokine typically enhances or modifies the immune response by activating or enhancing the activity of cells of the immune system and is not itself immunogenic to the host.

It follows from the results presented herein that a variety of cytokines will find use in the present invention. Exemplary cytokines for use in practicing the invention include but are not limited to IFN-alpha, IFN-beta, and IFN-gamma, interleukins (e.g., IL-1 to IL-29, in particular, IL-2, IL-7, IL-12, IL-15 and IL-18), tumor necrosis factors (e.g., TNF-alpha and TNF-beta), erythropoietin (EPO), MIP3a, macrophage colony stimulating factor (M-CSF), granulocyte colony stimulating factor (G-CSF) and granulocyte-macrophage colony stimulating factor (GM-CSF). The cytokine may be from any source, however, optimally the cytokine is of murine or human origin (a native human or murine cytokine) or is a sequence variant of such a cytokine, so long as the cytokine has a sequence with substantial homology to the human form of the cytokine and exhibits a similar activity on the immune system. It follows that cytokines with substantial homology to the human forms of IFN-alpha, IFN-beta, and IFN-gamma, IL-1 to IL-29, TNF-alpha, TNF-beta, EPO, MIP3a, ICAM, M-CSF, G-CSF and GM-CSF are useful in practicing the invention, so long as the homologous form exhibits the same or a similar effect on the immune system. Proteins that are substantially similar to any particular cytokine, but have relatively minor changes in protein sequence find use in the present invention. It is well known that small alterations in protein sequence may not disturb the functional activity of a protein molecule, and thus proteins can be made that function as cytokines in the present invention but differ slightly from current known or native sequences.

Variant Sequences

Homologues and variants of native human or murine cytokines and antigen presenting cell (APC) activator are included within the scope of the invention. As used herein, the term "sequence identity" means nucleic acid or amino acid sequence identity between two or more aligned sequences and is typically expressed as a percentage ("%"). The term "% homology" is used interchangeably herein with the term "% identity" or "% sequence identity" and refers to the level of nucleic acid or amino acid sequence identity between two or more aligned sequences, when aligned using a sequence alignment program. For example, as used herein, 80% homology means the same thing as 80% sequence identity determined by a defined algorithm, and accordingly a homologue of a given sequence typically has greater than 80% sequence identity over a length of the given sequence. Preferred levels of sequence identity include, but are not limited to, 80, 85, 88, 89, 90, 91, 92, 93, 94, 95, 96, 97, 98 or 99% or more sequence identity to a native cytokine or presenting cell (APC) activator amino acid or nucleic acid sequence, as described herein.

Exemplary computer programs that can be used to determine the degree of identity between two sequences include, but are not limited to, the suite of BLAST programs, e.g., BLASTN, BLASTX, TBLASTX, BLASTP and TBLASTN, all of which are publicly available on the Internet. See, also, Altschul, S. F. et al. Mol. Biol. 215:403-410, 1990 and Altschul, S. F. et al. Nucleic Acids Res. 25:3389-3402, 1997, expressly incorporated by reference herein. Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. In determining sequence identity, both BLASTN and BLASTX (i.e. version 2.2.5) are run using default parameters of an open gap penalty of 11.0, and an extended gap penalty of 1.0, and utilize the BLOSUM-62 matrix. [See, Altschul, et al., 1997, supra.] A preferred alignment of selected sequences in order to determine "% identity" between two or more sequences, is performed using for example, the CLUSTAL-W program in Mac Vector version 6.5, operated with default parameters, including an open gap penalty of 10.0, an extended gap penalty of 0.1, and a BLOSUM 30 similarity matrix.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about TM-5° C. (5° below the Tm of the probe) "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe, while high stringency conditions are used to identify sequences having about 80% or more sequence identity with the probe. An example of high stringency conditions includes hybridization at about 42° C. in 50% formamide, 5×SSC, 5×Denhardt's solution, 0.5% SDS and 100 fig/ml denatured carrier DNA followed by washing two times in 2×SSC and 0.5% SDS at room temperature and two additional times in O.1×SSC and 0.5% SDS at 42° C. Moderate and high stringency hybridization conditions are well known in the art. See, for example, Sambrook, et al, 1989, Chapters 9 and 11, and in Ausubel, F. M., et al., 1993, (expressly incorporated by reference herein).

APC Activators or Treatments

As detailed herein, the present invention is directed to a method of improving an individual's immune response to cancer (e.g., a target cancer antigen or antigens) by co-administering a cytokine-expressing cellular immunotherapy (e.g., GM-CSF) and at least one additional antigen presenting cell (APC) activator or treatment to a patient with cancer.

Antigen presenting cell (APC) activators or treatments for use in practicing the invention include, but are not limited to, adhesion or accessory molecules, other biological response modifiers, chemotherapeutic agents, radiation treatment and combinations thereof.

Embodiments of the present invention include the administration of the combination of a cytokine-expressing cellular immunotherapy and at least one additional antigen presenting cell (APC) activator. Antigen presenting cell (APC) activators for use in practicing the invention include LAG-3.

Immune regulation is believed to involve a balance between T-helper 1 (Th 1) and T-helper 2 (Th2) cell activity. Th1 cells drive the type-1 pathway ("cellular immunity") to fight viruses and other intracellular pathogens, eliminate cancerous cells, and stimulate delayed-type hypersensitivity (DTH) skin reactions and Th2 cells drive the type-2 pathway ("humoral immunity") and up-regulate antibody production to fight extracellular organisms. Overactivation of either activity can cause disease, and either pathway can down-regulate the other.

As these two arms of the immune system are mutually inhibitory, through the actions of cytokines produced by TH1 and TH2 cells, a strong TH2 (pro-inflammatory) immune response, such as that induced under conditions of stress or chemical exposure, will suppress the production of TH1 cytokines, which play a vital role in strengthening the cellular immune response and thus the body's ability to defend itself against pathogens and carcinogenic agents.

A clinically effective cancer immunotherapy requires the generation and expansion of specific cytotoxic T lymphocytes (CTL) able to proliferate and/or secrete Th1-type cytokines such as IL-2, IFNγ or TNF-α after antigen-specific stimulation. The immune response is believed to involve two ligands that are expressed on activated T cells and bind to non-toll-like receptors (TLRs) expressed on dendritic cells. These are the CD40L and lymphocyte activation gene-3 (LAG-3 or CD223) human proteins. Soluble forms have been tested at the preclinical and/or clinical stage as adjuvants for immunological immunotherapies. Clinical development of soluble CD40L (sCD40L) has been hampered by an increased risk of thrombosis due to direct platelet activation by sCD40L (Brignone, C. et al., Journal of Immune Based Therapies and Immunotherapies 2007, 5:5).

Some forms of soluble LAG-3 (sLAG-3) can bind to MHC class II molecules and can induce dendritic cells (DC) to mature and migrate to secondary lymphoid organs where they can prime naïve CD4-helper and CD8-cytotoxic T cells leading to tumour rejection (Prigent P. et al., Eur J Immunol 1999, 29:3867-3876).

LAG-3 (CD223) is described as having a natural high affinity ligand for MHC class II, is known to induce maturation of monocyte-derived dendritic cells in vitro and is used as a immunotherapy adjuvant to induce CD4 T helper type 1 responses and CD8 T-cell responses in vivo (Brignone, C. et al., J Immune Based Ther Immunotherapies. 2007; 5: 5). Further information regarding LAG 3 and its use as an immunostimulant may be found in Triebel et al., 1990, *J. Exp. Med.* 171:1393-1405; Triebel., 2003, *Trends Immunol* 24:619-622; and Huard et al., 1997, *Proc. Natl. Acad. Sci. USA* 94:5744-5749

In some embodiments, the LAG-3 that is administered comprises the amino acid sequence of SEQ ID NO.: 1. In some embodiments, the LAG-3 comprises at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, or about 500 contiguous amino acids selected from SEQ ID NO.: 1.

In some embodiments, the LAG-3 that is administered is a fragment of LAG-3 as defined herein. In certain embodiments, the LAG-3 fragment comprises at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, or about 500 contiguous amino acids selected from SEQ ID NO.: 1. In certain embodiments, the LAG-3 fragment does not comprise the entire amino acid sequence of SEQ ID NO.:1. In certain embodiments, the LAG-3 fragment consists essentially of at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, or about 500 contiguous amino acids selected from SEQ ID NO.: 1. In certain embodiments, the LAG-3 fragment consists of at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, or about 500 contiguous amino acids selected from SEQ ID NO.: 1.

In some embodiments, the LAG-3 that is administered is a LAG-3 derivative as defined herein. In certain embodiments, the LAG-3 derivative comprises at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, or about 500 contiguous amino acids selected from SEQ ID NO.:1. In certain embodiments, the LAG-3 derivative does not comprise the entire amino acid sequence of SEQ ID NO.: 1. In certain embodiments, the LAG-3 derivative is a fusion protein. In certain embodiments, the LAG-3 derivative comprises one or more immunoglobin constant regions. In certain embodiments, the LAG-3 derivative comprises the CH2 and CH3 domains of a immunoglobulin heavy chain. In certain embodiments, the CH2 and CH3 domains of the immunoglobulin heavy chain are from an IgG4 immunoglobulin. In certain embodiments, the CH2 and CH3 domains of the immunoglobulin heavy chain are from an IgG1 immunoglobulin. In a particular embodiment, the LAG-3 derivative has an amino acid sequence that is SEQ ID NO.:2.

In some embodiments, the LAG-3 that is administered is a homolog of LAG-3 as defined herein. In certain embodiments, the LAG-3 homolog comprises an amino acid sequence that is homologous to at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, or about 500 contiguous amino acids selected from SEQ ID NO.:1. In certain embodiments, the LAG-3 homolog is about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 99.5% homologous to the amino acid sequence selected from SEQ ID NO.: 1.

Cellular Immunotherapy Combinations

Granulocyte-macrophage colony stimulating factor (GM-CSF) is a cytokine produced by fibroblasts, endothelial cells, T cells and macrophages. This cytokine has been shown to induce the growth of hematopoetic cells of granulocyte and macrophage lineages. In addition, the cytokine activates the antigen processing and presenting function of dendritic cells, which are the major antigen presenting cells (APC) of the immune system. Results from animal model experiments have convincingly shown that GM-CSF producing tumor cells are able to induce an immune response against parental, non-transduced tumor cells.

Autologous and allogeneic cancer cells that have been genetically modified to express a cytokine, e.g., GM-CSF, followed by readministration to a patient for the treatment of cancer are described in U.S. Pat. Nos. 5,637,483, 5,904,920 and 6,350,445, expressly incorporated by reference herein. A form of GM-CSF-expressing genetically modified cancer cells or a "cytokine-expressing cellular immunotherapy" for the treatment of pancreatic cancer is described in U.S. Pat. Nos. 6,033,674 and 5,985,290, expressly incorporated by reference herein. A universal immunomodulatory cytokine-expressing bystander cell line is described in U.S. Pat. No. 6,464,973, expressly incorporated by reference herein. Clinical trials employing GM-CSF-expressing autologous or allogeneic cellular immunotherapies have been undertaken for treatment of prostate cancer, melanoma, lung cancer, pancreatic cancer, renal cancer, and multiple myeloma. A number of these trials are currently ongoing, however, and the question still remains open as to whether the immune response to GM-CSF expressing cells alone will be sufficiently powerful to slow or eradicate large or fast growing malignancies.

The present invention this provides an improved method of stimulating an immune response to cancer in a mammalian, preferably a human, patient. Desirably, the method effects a systemic immune response, i.e., a T-cell response and/or a B-cell response, to the cancer. In some embodiments, the method comprises administering to the patient a cytokine-expressing cellular immunotherapy and at least one additional antigen presenting cell (APC) activator or treatment, wherein the cellular immunotherapy comprises cells which express a cancer antigen or various cancer antigens. The cancer antigen/antigens can be one of the antigens of the cancer found in the patient under treatment. The cells can be rendered proliferation incompetent, such as e.g., by irradiation. Upon administration of the composition, an immune response to the cancer can be elicited or enhanced. In one approach, the cytokine-expressing cellular immunotherapy combination comprises a single population of cells that is modified to express a cytokine and at least one additional antigen presenting cell (APC) activator. In another approach, the immunotherapy comprises two or more populations of cells individually modified to express one component of the immunotherapy. In yet another approach, the cytokine-expressing cellular immunotherapy combination comprises a population of cells that is modified to express a cytokine which is administered in combination with at least one additional antigen presenting cell (APC) activator or treatment.

In general, a cytokine-expressing cellular immunotherapy combination for use in practicing the invention comprises tumor cells selected from the group consisting of autologous tumor cells, allogeneic tumor cells and tumor cell lines (i.e., bystander cells).

In some embodiments, the cells of the cytokine-expressing cellular immunotherapy combination are cryopreserved prior to administration. In one aspect of the invention, the cells of the cytokine-expressing cellular immunotherapy combination are administered to the same individual from whom they were derived (autologous). In another aspect of the invention, the cells of the cytokine-expressing cellular immunotherapy combination and the tumor are derived from different individuals (allogeneic or bystander). In a preferred approach, the tumor being treated is selected from the group consisting of cancer of the bladder, breast, colon, kidney, liver, lung, ovary, cervix, pancreas, rectum, prostate, stomach, epidermis, a hematopoietic tumor of lymphoid or myeloid lineage, a tumor of mesenchymal origin such as a fibrosarcoma or rhabdomyosarcoma, melanoma, teratocarcinoma, neuroblastoma, glioma, adenocarcinoma and non-small lung cell carcinoma.

In one aspect of the invention, the cells of the cytokine-expressing cellular immunotherapy combination comprises gene-modified cells of one type for the expression of the cytokine and of another different type for expression of the one or more additional antigen presenting cell (APC) activator. By way of example, in one approach, the cytokine-expressing cellular immunotherapy is provided as an allogeneic or bystander cell line while the one or more additional cancer therapeutic agents is expressed by autologous cells. In another approach, the one or more additional antigen presenting cell (APC) activator is expressed by an allogeneic or bystander cell line while the cytokine (i.e., GM-CSF) is expressed by autologous cells.

In previous studies, a direct comparison of murine tumor cells transduced with various cytokines demonstrated that GM-CSF-secreting tumor cells induced the best overall antitumor protection. In one preferred embodiment, the cytokine expressed by the cytokine-expressing cellular immunotherapy of the invention is GM-CSF. The preferred coding sequence for GM-CSF is the genomic sequence described in Huebner K. et al, Science 230(4731): 1282-5, 1985. Alternatively the cDNA form of GM-CSF finds utility in practicing the invention (Cantrell et al., Proc. Natl. Acad. Sci., 82, 6250-6254, 1985).

Prior to administration, the cells of a cytokine-expressing cellular immunotherapy combination of the invention are rendered proliferation incompetent. While a number of means of rendering cells proliferation incompetent are known, irradiation is the preferred method. Preferably, the cytokine-expressing cellular immunotherapy combination is irradiated at a dose of from about 50 to about 200 rads/min, even more preferably, from about 120 to about 140 rads/min prior to administration to the patient. Most importantly, the cells are irradiated with a total radiation dose sufficient to inhibit growth of substantially 100% of the cells, from further proliferation. Thus, desirably the cells are irradiated with a total dose of from about 10,000 to 20,000 rads, optimally, with about 15,000 rads.

Autologous

The use of autologous cytokine-expressing cells in a immunotherapy of the invention provides advantages since each patient's tumor expresses a unique set of tumor antigens that can differ from those found on histologically-similar, MHC-matched tumor cells from another patient. See, e.g., Kawakami et al, J. Immunol, 148, 638-643 (1992); Darrow et al., J. Immunol., 142, 3329-3335 (1989); and Horn et al., J. Immunother., 10, 153-164 (1991). In contrast, MHC-matched tumor cells provide the advantage that the patient need not be taken to surgery to obtain a sample of their tumor for immunotherapy production.

In one preferred aspect, the present invention comprises a method of treating cancer by carrying out the steps of: (a) obtaining tumor cells from a mammal, preferably a human, harboring a tumor; (b) modifying the tumor cells to render them capable of producing a cytokine or an increased level of a cytokine naturally produced by the cells and at least one additional cancer therapeutic agent relative to unmodified tumor cells; (c) rendering the modified tumor cells proliferation incompetent; and (d) readministering the modified tumor cells to the mammal from which the tumor cells were obtained or to a mammal with the same MHC type as the mammal from which the tumor cells were obtained. The administered tumor cells are autologous or MHC-matched to the host.

The same autologous tumor cells may express both a cytokine and antigen presenting cell (APC) activator or a cytokine and one or more antigen presenting cell (APC) activator(s) may be expressed by a different autologous tumor cell population. In one aspect of the invention, an autologous tumor cell is modified by introduction of a vector comprising a nucleic acid sequence encoding a cytokine, operably linked to a promoter and expression/control sequences necessary for expression thereof. In another aspect, the same autologous tumor cell is modified by introduction of a vector comprising a nucleic acid sequence encoding at least one additional antigen presenting cell (APC) activator operably linked to a promoter and expression/control sequences necessary for expression thereof. In a further aspect, a second autologous tumor cell is modified by introduction of a vector comprising a nucleic acid sequence encoding at least one additional cancer antigen presenting cell (APC) activator operably linked to a promoter and expression/control sequences necessary for expression thereof. The nucleic acid sequence encoding the cytokine and additional antigen presenting cell (APC) activator(s) may be introduced into the same or a different autologous tumor cell using the same or a different vector. The nucleic acid sequence encoding the cytokine or antigen presenting cell (APC) activator or may not further comprise a selectable marker sequence operably linked to a promoter.

Allogeneic

Researchers have sought alternatives to autologous and MHC-matched cells as tumor immunotherapies, as reviewed by Jaffee et al., Seminars in Oncology, 22, 81-91 (1995). Early tumor immunotherapy strategies were based on the understanding that the vaccinating tumor cells function as the antigen presenting cells (APCs) and present tumor antigens by way of their MHC class I and II molecules, and directly activate the T cell arm of the immune system. The results of Huang et al. (Science, 264, 961-965, 1994), indicate that professional APCs of the host rather than the vaccinating tumor cells prime the T cell arm of the immune system by secreting cytokine(s) such as GM-CSF such that bone marrow-derived APCs are recruited to the region of the tumor. These results suggest that it may not be necessary or optimal to use autologous or MHC-matched tumor cells in order to elicit an anti-cancer immune response and that the transfer of allogeneic MHC genes (from a genetically dissimilar individual of the same species) can enhance tumor immunogenicity. More specifically, in certain cases, the rejection of tumors expressing allogeneic MHC class I molecules resulted in enhanced systemic immune responses against subsequent challenge with the unmodified parental tumor, as reviewed in Jaffee et al., supra, and Huang et al., supra.

As described herein, a "tumor cell line" comprises cells that were initially derived from a tumor. Such cells typically are transformed (i.e., exhibit indefinite growth in culture).

In one preferred aspect, the invention provides a method for treating cancer by carrying out the steps of: (a) obtaining a tumor cell line; (b) modifying the tumor cell line to render the cells capable of producing an increased level of a cytokine alone or in combination with at least one additional antigen presenting cell (APC) activator relative to the unmodified tumor cell line; (c) rendering the modified tumor cell line proliferation incompetent; and (d) administering the tumor cell line to a mammalian host having at least one tumor that is the same type of tumor as that from which the tumor cell line was obtained or wherein the tumor cell line and host tumor express at least one common antigen. The administered tumor cell line is allogeneic and is not MHC-matched to the host. Such allogeneic lines provide the advantage that they can be prepared in advance, characterized, aliquoted in vials containing known numbers of cytokine-expressing cells and stored such that well-characterized cells are available for administration to the patient. Methods for the production of gene-modified allogeneic cells are described for example in International Patent Publication No. WO 00/72686A1, expressly incorporated by reference herein.

In one approach to preparing a cytokine-expressing cellular immunotherapy comprising gene-modified allogeneic cells, cytokine and antigen presenting cell (APC) activator-encoding nucleic acid sequences are introduced into a cell line that is an allogeneic tumor cell line (i.e., derived from an individual other than the individual being treated). In another approach, cytokine and antigen presenting cell (APC) activator encoding nucleic acid sequences are introduced into separate (i.e. different) allogeneic tumor cell lines. The cell or population of cells may be from a tumor cell line of the same type as the tumor or cancer being treated. The tumor and/or tumor cell line may be from any form of cancer, including, but not limited to, carcinoma of the bladder, breast, colon, kidney, liver, lung, ovary, cervix, pancreas, rectum, prostate, stomach, epidermis, a hematopoietic tumor of lymphoid or myeloid lineage, a tumor of mesenchymal origin such as a fibrosarcoma or rhabdomyosarcoma, melanoma, teratocarcinoma, neuroblastoma, glioma, adenocarcinoma, and non-small lung cell carcinoma.

In one aspect of the invention, the allogeneic tumor cell is modified by introduction of a vector comprising a nucleic acid sequence encoding a cytokine, operably linked to a promoter and expression control sequences necessary for expression thereof. In another aspect, the same allogeneic tumor cell or a second allogeneic tumor cell is modified by introduction of a vector comprising a nucleic acid sequence encoding at least one additional antigen presenting cell (APC) activator operably linked to a promoter and expression control sequences necessary for expression thereof. The nucleic acid sequence encoding the cytokine and additional antigen presenting cell (APC) activator(s) may be introduced into the same or a different allogeneic tumor cell using the same or a different vector. The nucleic acid sequence encoding the cytokine or antigen presenting cell (APC) activator may or may not further comprise a selectable marker sequence operably linked to a promoter. Desirably, the allogeneic cell line expresses GM-CSF in a range from 200-1000 ng/$10^6$ cells/24 h. Preferably, the universal bystander cell line expresses at least about 200 ng GM-CSF/$10^6$ cells/24 hours.

In practicing the invention, one or more allogeneic cell lines can be incubated with an autologous cancer antigen, e.g., an autologous tumor cell (which together comprise an allogeneic cell line composition), then the allogeneic cell line composition can be administered to the patient. Typically, the cancer antigen can be provided by (on) a cell of the cancer to be treated, i.e., an autologous cancer cell. In such cases, the composition can be rendered proliferation-incompetent by irradiation, wherein the allogeneic cells and cancer cells are plated in a tissue culture plate and irradiated at room temperature using a Cs source, as detailed above. The ratio of allogeneic cells to autologous cancer cells in a given administration will vary dependent upon the combination.

Any suitable route of administration can be used to introduce an allogeneic cell line composition into the patient. Preferably, the composition is administered subcutaneously or intratumorally.

The use of allogeneic cell lines in practicing present invention enables administration of a cytokine-expressing allogeneic cell line and at least one additional antigen presenting cell (APC) activator (expressed by the same or a different cell line) to a patient with cancer, together with an autologous cancer antigen. This treatment can result in an effective immune response to a tumor. This approach advantageously obviates the need to culture and transduce autologous tumor cells for each patient, eliminating the problem of variable and inefficient transduction efficiencies.

Bystander

In one further aspect, the present invention provides a universal immunomodulatory cytokine-expressing bystander cell line and a bystander cell line that expresses at least one additional antigen presenting cell (APC) activator. The same universal bystander cell line may express both a cytokine and antigen presenting cell (APC) activator or each may be expressed by a different universal bystander cell line. The universal bystander cell line comprises cells which either naturally lack major histocompatibility class I (MHC-I) antigens and major histocompatibility class II (MHC-II) antigens or have been modified so that they lack MHC-I antigens and MHC-II antigens. In one aspect of the invention, a universal bystander cell line is modified by introduction of a vector comprising a nucleic acid sequence encoding a cytokine operably linked to a promoter and expression control sequences necessary for expression thereof. In another aspect, the same universal bystander cell line or a second universal bystander cell line is modified by introduction of a vector comprising a nucleic acid sequence encoding at least one additional antigen presenting cell (APC) activator operably linked to a promoter and expression control sequences necessary for expression thereof. The nucleic acid sequence encoding the cytokine and additional antigen presenting cell (APC) activator(s) may be introduced into the same or a different universal bystander cell line using the same or a different vector. In some cases, the bystander approach is combined with the autologous or allogeneic approach. For example, an autologous, allogeneic or bystander cell line encoding a cytokine may be combined with an autologous, allogeneic or bystander cell line encoding one or more antigen presenting cell (APC) activator(s). The nucleic acid sequence encoding the cytokine or antigen presenting cell (APC) activator may or may not further comprise a selectable marker sequence operably linked to a promoter. Any combination of cytokine(s) and antigen presenting cell (APC) activator(s) that stimulate an anti-tumor immune response finds utility in the practice of the present invention. The universal bystander cell line preferably grows in defined, e.g., serum-free, medium, preferably as a suspension.

An example of a preferred universal bystander cell line is K562 (ATCC CCL-243; Lozzio et al, Blood 45(3): 321-334 (1975); Klein et al., Int. J. Cancer 18: 421-431 (1976)). A detailed description of human bystander cell lines is described for example in U.S. Pat. No. 6,464,973 and International Patent Publication No. WO 9938954. Desirably, the universal bystander cell line expresses the cytokine, e.g., GM-CSF in the range from 200-1000 ng/$10^6$ cells/24 h. Preferably, the universal bystander cell line expresses at least about 200 ng GM-CSF/$10^6$ cells/24 hours.

In practicing the invention, the one or more universal bystander cell lines can be incubated with an autologous cancer antigen, e.g., an autologous tumor cell (which together comprise a universal bystander cell line composition), then the universal bystander cell line composition can be administered to the patient. Any suitable route of administration can be used to introduce a universal bystander cell line composition into the patient. Preferably, the composition is administered subcutaneously or intratumorally.

Typically, the cancer antigen can be provided by (on) a cell of the cancer to be treated, i.e., an autologous cancer cell. In such cases, the composition can be rendered proliferation-incompetent by irradiation, wherein the bystander cells and cancer cells are plated in a tissue culture plate and irradiated at room temperature using a Cs source, as detailed above.

The ratio of autologous bystander cells to autologous cancer cells in a given administration will vary dependent upon the combination. With respect to GM-CSF-producing bystander cells, the ratio of bystander cells to autologous cancer cells in a given administration should be such that at least 36 ng GM-CSF/$10^6$ cells/24 hrs is produced, as the therapeutic effect may be decreased if the concentration of GM-CSF is less than this. In addition to the GM-CSF threshold, the ratio of bystander cells to autologous cancer cells should not be greater than 1:1. Appropriate ratios of bystander cells to tumor cells or tumor antigens can be determined using routine methods in the art.

The use of bystander cell lines in practicing present invention enables administration of a cytokine-expressing bystander cell line and at least one additional antigen presenting cell (APC) activator (expressed by the same or a different cell line) to a patient with cancer, together with an autologous cancer antigen. This treatment can result in an effective immune response to a tumor. This approach advantageously obviates the need to culture and transduce autologous tumor cells for each patient, eliminating the problem of variable and inefficient transduction efficiencies.

Evaluation of Combinations in Animal Models

B16F10 Melanoma Model

In one approach, the efficacy of cytokine-expressing cellular immunotherapy combination can be evaluated by carrying out animal studies in the syngeneic B16F10 melanoma tumor model in the treatment setting. See, e.g., Griswold D P Jr., Cancer Chemother Rep 2; 3(1):315-24, 1972 and Berkelhammer J et al, Cancer Res 42(8):3157-63, 1982. The murine melanoma cell line B16 is a well-defined cell line which is weakly immunogenic in syngeneic C57B16 mice and therefore readily forms tumors in C57BL6 mice. Furthermore, several tumor associated antigens have been identified in this model which allow one to monitor tumor specific as well as antigen specific immune responses. In addition, several murine-specific reagents are commercially available and are used to monitor anti-tumor immune responses in the various immunotherapy strategies. A typical study in the B16F10 melanoma tumor model makes use of at least 6 and generally 10-15 mice per group in order to obtain statistically significant results. Statistical significance can be evaluated using the Student's t-test.

Treatment of C57BL/6 mice with irradiated GM-CSF-secreting B16F10 tumor cells stimulates potent, long-lasting and specific anti-tumor immunity that prevents tumor growth in most mice subsequently challenged with wild-type B16F10 cells. However, this protection is less effective when GM-CSF-producing tumor cell immunotherapies are administered to mice with preexisting tumor burden. In carrying out studies using the B16F10 melanoma tumor model, female C57BL/6 mice are obtained from Taconic and are 6-8 weeks old at the start of each experiment. In a typical experiment, mice are injected with $1 \times 10^5$ B16BF10 cells on day 0 subcutaneously in a dorsal/anterior location. On day 3, mice are vaccinated in a ventral/posterior location with $1-3 \times 10^6$ irradiated (10,000 rads) B16F10 or cytokine-expressing cellular immunotherapy. Mice are followed for tumor development and survival. After 14-21 days, mice are sacrificed and their tumor burden assessed by harvesting the mice lungs and counting the surface tumor metastasis and measuring the weight of the lung. An alternative B16F10 melanoma tumor model involves subcutaneous injection of B16F10 tumor cells. A typical in vivo study in the B16F10 melanoma tumor model employs the following groups: HBSS only (negative control); irradiated B16F10/HBSS (control): cytokine-expressing cellular immunotherapy/HBSS; (cellular immunotherapy monotherapy control); additional antigen presenting cell (APC) activator or treatment (therapeutic agent/treatment monotherapy control); cytokine-expressing cellular immunotherapy plus antigen presenting cell (APC) activator or treatment (FIGS. 1A-1D).

Previous experiments have demonstrated that HBSS or irradiated B16F10 alone do not protect challenged mice from tumor formation. GM-CSF-expressing cellular immunotherapies alone were shown to protect from 10-20% of the challenged mice. The combination of a cytokine-expressing cellular immunotherapy plus at least one additional antigen presenting cell (APC) activator or treatment is expected to increase the efficacy of anti-tumor protection. The degree of protection depends on several factors such as the expression level of the additional antigen presenting cell (APC) activator and the cytokine-expressing cellular immunotherapy, the level of treatment (i.e. dose of the agent or the frequency and strength of radiation) and the relative timing and route of administration of the additional cancer antigen presenting cell (APC) activator (e.g., as transfected cells or as a protein or chemical entity) relative to the timing of administration of the cytokine-expressing cellular immunotherapy.

Immunological Monitoring

Several tumor associated antigens have been identified which allow one to monitor tumor specific as well as antigen-specific immune responses. For example, tumor antigen-specific T cells can be identified by the release of IFN-gamma following antigenic restimulation in vitro (Hu, H-M. et al, Cancer Research, 2002, 62; 3914-3919). Yet another example of new methods used to identify tumor antigen-specific T cells is the development of soluble MHC I molecules also known as MHC tetramers (Beckman Coulter, Immunomics), reported to be loaded with specific peptides shown to be involved in an anti-tumor immune response. Examples within the B16F10 melanoma tumor model include but are not limited to ge100, Trp2, Trp-1, and tyrosinase. Similar melanoma-associated antigens have been identified in humans. Such tools provide information that can then be translated into the clinical arena.

Assays for Efficacy of Combinations In Vivo Models

Tumor burden can be assessed at various time points after tumor challenge. Typically, spleens cells are assessed for CTL activity by in vitro whole cell stimulation for 5 days. Target cells are labeled with $^{51}Cr$ and co-incubated with splenic effector CTL and release of $^{51}Cr$ into the supernatants as an indicator of CTL lysis of target cells. On day 3 of in vitro stimulated CTL supernatants are tested for IFN-gamma production by CTL. In brief, wells are coated with coating antibody specific for IFN-gamma, supernatant is then added to wells, and IFN-gamma is detected using an IFN-gamma specific detecting antibody. IFN-gamma can also be detected by flow cytometry, in order to measure cell-specific IFN-gamma production.

Another indication of an effective anti-tumor immune response is the production of effector cytokines such as TNF-alpha, IL-2, and IFN-gamma upon restimulation in vitro. Cytokine levels were measured in supernatants from spleen cells or draining lymph node (dLN) cells restimulated in vitro for 48 hours with irradiated GM-CSF-expressing cells.

A further method used to monitor tumor-specific T cell responses is via intracellular cytokine staining (ICS). ICS can be used to monitor tumor-specific T-cell responses and to identify very low frequencies of antigen-specific T-cells. Because ICS is performed on freshly isolated lymphocytes within 5 hours of removal, unlike the CTL and cytokine release assays, which often require 2-7 days of in vitro stimulation, it can be used to estimate the frequency of tumor antigen-specific T-cells in vivo. This provides a powerful technique to compare the potency of different tumor immunotherapy strategies. ICS has been used to monitor T-cell responses to melanoma-associated antigens such as gp1OO and Trp2 following various melanoma immunotherapy strategies. Such T-cells can be identified by the induction of intracellular IFN-gamma expression following stimulation with a tumor-specific peptide bound to MHC I.

Xenogen Imaging of Tumor Models

In some studies, in vivo luminescence of tumor bearing mice is monitored by monitoring of B16F10-luciferase (Xenogen Inc.) injected mice. In brief, Balb/c nu/nu mice are injected with $5 \times 10^4$ or $2 \times 10^5$ cells of B16F10-luc cells via tail vein on day 0. Mice are monitored for tumor burden when necessary by intra-peritoneal injection of excess luciferin substrate at 1.5 mg/g mice weight. In a typical analysis, twenty minutes after substrate injection, mice are anesthesized and monitored for in vivo luminescence with Xenogen IVIS Imaging System (Xenogen Inc.) luminescence sensitive CCD camera by dorsal or ventral position. Data is collected and analyzed by Living Image 2.11 software.

Cytokine-Expressing Cellular Immunotherapy Combinations

The present invention relates, in part, to combinations of a cytokine-expressing cellular immunotherapy plus at least one additional antigen presenting cell (APC) activator or treatment. The activator or treatment may be a chemotherapeutic agent, an agent that modulates the immune response to a cancer antigen, radiation, etc. Exemplary embodiments of the invention, include, but are not limited to a cytokine-expressing cellular immunotherapy plus LAG-3.

Figure 4A:
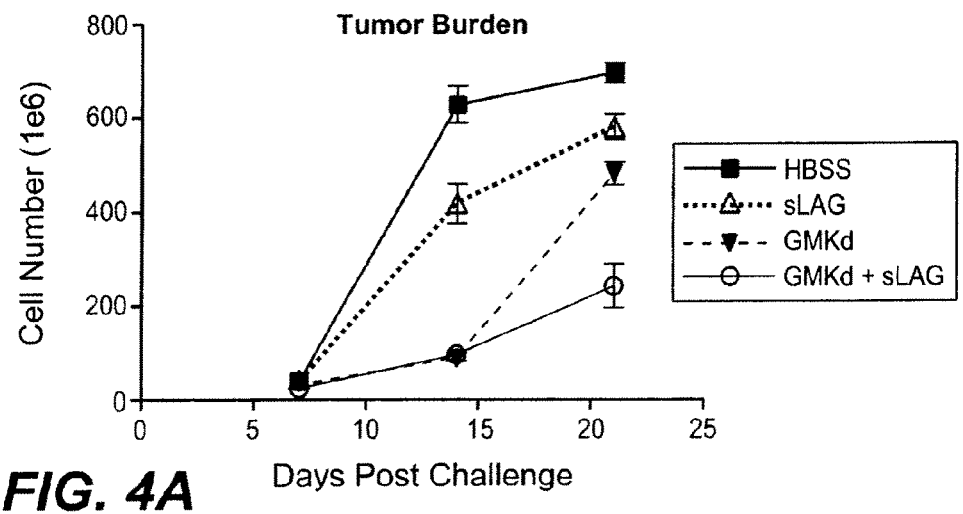
FIG. 4A illustrates tumor burden following treatment with GM-CSF-secreting tumor cells or LAG-3 or a combination of LAG-3 plus GM-CSF-secreting tumor cells. On day 0, mice were inoculated SC with live B16 tumor cells. On day 3, mice were immunized with $1 \times 10^6$ irradiated GM-CSF-secreting tumor cells as immunotherapy alone or immunotherapy was followed by daily injections of 0.1 μg of LAG-3 on days 5 to 7 as combination therapy. LAG-3 monotherapy-treated mice were treated on days 5 to 7. At indicated timepoints, tumors (n=5) were removed, digested, and the cells counted.
Figure 4B:
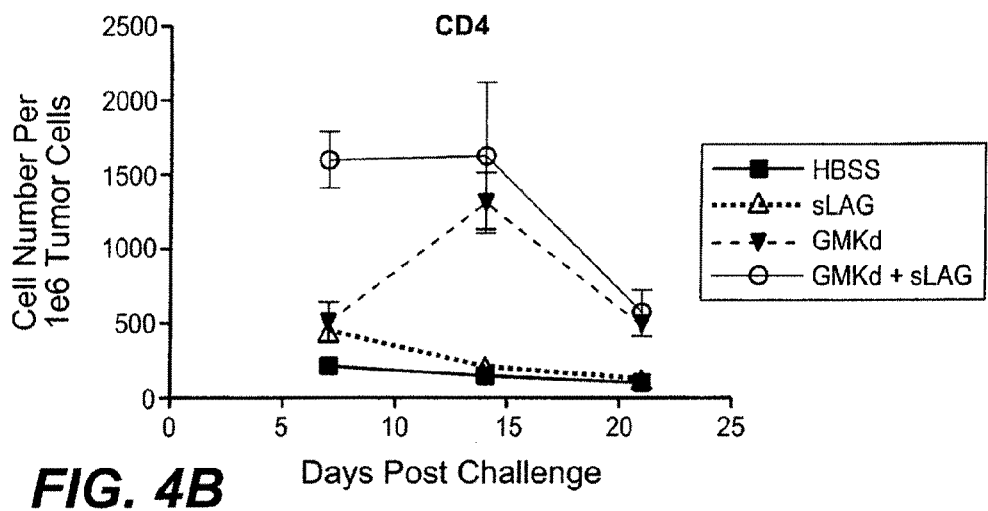
FIG. 4B illustrates changes in the number of CD4$^+$T cells/$1 \times 10^6$ tumor cells following treatment with GM-CSF-secreting tumor cell or LAG-3 or LAG-3 plus GM-CSF-secreting tumor cell combination. On day 0, mice were inoculated SC with live B16 tumor cells. On day 3, mice were immunized with $1 \times 10^6$ irradiated GM-CSF-secreting tumor cells as immunotherapy alone or immunotherapy was followed by daily injections of 0.1 μg of LAG-3 on days 5 to 7 as combination therapy. LAG-3 monotherapy-treated mice were treated on days 5 to 7. At indicated timepoints, tumors (n=5) were removed, digested, stained and evaluated by flow cytometry.
Figure 4C:
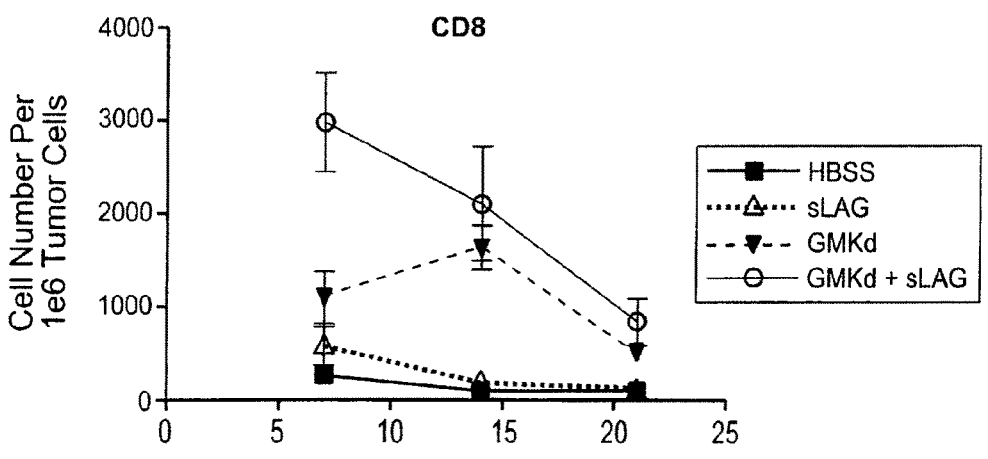
FIG. 4C illustrates changes in the number of CD8$^{+T}$ cells/$1 \times 10^6$ tumor cells following treatment with GM-CSF-secreting tumor cell or LAG-3 or LAG-3 plus GM-CSF-secreting tumor cell combination. On day 0, mice were inoculated SC with live B16 tumor cells. On day 3, mice were immunized with $1 \times 10^6$ irradiated GM-CSF-secreting tumor cells as immunotherapy alone or immunotherapy was followed by daily injections of 0.1 μg of LAG-3 on days 5 to 7 as combination therapy. LAG-3 monotherapy-treated mice were treated on days 5 to 7. At indicated timepoints, tumors (n=5) were removed, digested, stained and evaluated by flow cytometry.

Co-Stimulatory Molecules in Combination with Cytokine-Expressing Cellular Immunotherapies In natural immune responses, CD4+T helper (Th) cells, reactive with peptide antigens presented by MHC class II molecules on dendritic cells (DC), can drive the maturation of DC which is required for induction of CD8+CTL immunity. Proper induction, expansion and maintenance of CTL responses are achieved through the interaction between CD4+ T cells, DC and CD8+ T cells. While not intending to be bound to any particular theory or mechanism of action, the cells to a large extent are believed to operate through up-regulation of CD40L, which interacts with DC-expressed CD40 to effect DC maturation. CD80/CD86 expressed by mature or activated DC can effect CTL induction by interaction with the CS28 costimulatory receptor on CD8+ T cells. For maintenance and full expansion of CTL, interaction of the DC-expressed 4-1BB ligand with its receptor 4-1BB on CTL may also be important. DC activation may be triggered by e.g., agonistic anti-CD40 antibody or ligands of Toll-like receptors (TLR) such as LP5 (TLR4 ligand) or oligodeoxynucleotides containing CpG-motifs (TLR9 ligand). Rapid effector T cell infiltration into B16 tumor cells were detected in mice treated with GM-CSF-secreting tumor cells and LAG-3 (FIGS. 4B and 4C). Substantial increases in the number of CD4+cells and CD8+ cells per $1 \times 10^6$ tumor cells are shown in FIGS. 4B and 4C. In contrast, significant decreases in the number of tumor cells are shown in FIG. 4A.

Cytokine-Expressing Cellular Immunotherapies Plus Antigen Presenting Cell (APC) Activator Previous reports indicate that GM-CSF-secreting tumor cell immunotherapy provides partial protection of mice when either is used as a monotherapy for non-immunogenic tumors such as B16 melanoma. The results presented herein demonstrate that the combination of GM-CSF-secreting B16 tumor cells and antigen presenting cell (APC) activator acts synergistically, resulting in highly protective antitumor immune responses. In order to achieve the maximal synergistic effect of these two agents in clinical trials, it is essential to carefully evaluate possible treatment regimens in preclinical studies. In ongoing clinical trials GM-CSF-secreting tumor cell immunotherapies or antigen presenting cell (APC) activator are administered to patients repeatedly over a period of several months. In studies described herein, the efficacy of the combination was evaluated in preclinical studies following repeated administration of both antigen presenting cell (APC) activator and GM-CSF-secreting tumor cell immunotherapies. Example 1 details studies where a murine APC activator, i.e. LAG-3, was tested in the B16 melanoma tumor model with and without treatment with a cytokine-expressing cellular immunotherapy (GM-CSF-secreting B16F10 tumor cells; B16-GM) (FIG. 1A). The GM-CSF-secreting tumor cell immunotherapy was less effective than the combination therapy of antigen presenting cell (APC) activator and GM-CSF-secreting tumor cell immunotherapies (FIGS. 1A-1D).

Figure 2:
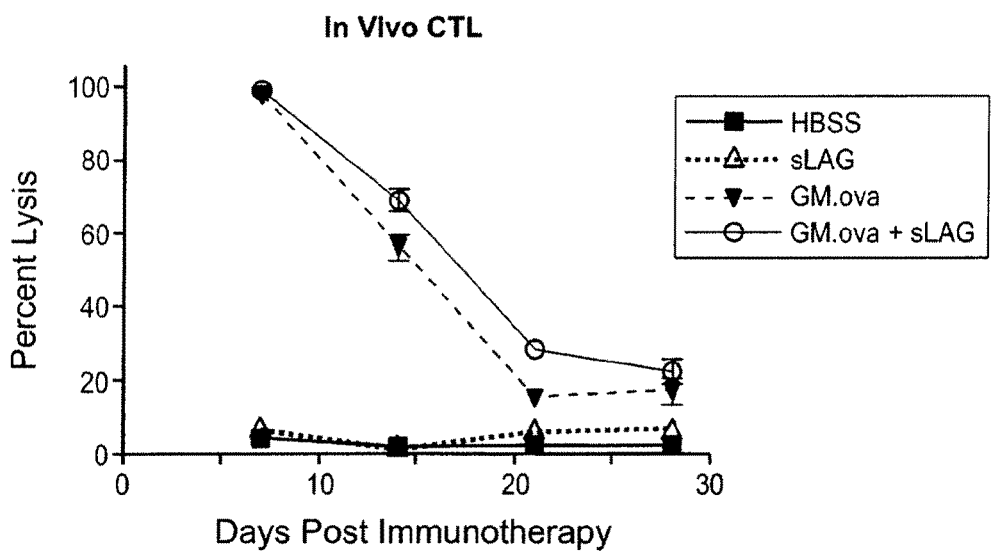
FIG. 2 illustrates cytolytic activity against B16 tumor cells in animals treated with GM-CSF-secreting tumor cell or LAG-3 or LAG-3 plus GM-CSF-secreting tumor cell combination. On day 0, mice were inoculated SC with live B16 tumor cells transduced to express the surrogate antigen ovalbumin (F10.ova). On day 3, mice were immunized with $1 \times 10^6$ irradiated GM-CSF-secreting F10.ova cells (GM.ova) as immunotherapy alone or immunotherapy was followed by daily injections of 0.1 μg of LAG-3 on days 5 to 7 as combination therapy. LAG-3 monotherapy-treated mice were treated on days 5 to 7. At indicated timepoints, mice were injected with CSFE-labeled syngenic splenocytes pulsed with ovalbumin derived peptide. 18 hours later, splenocytes were harvested and evaluated for cytolytic activity by measuring the ratio of CSFE-labeled cells.
Figure 3A:
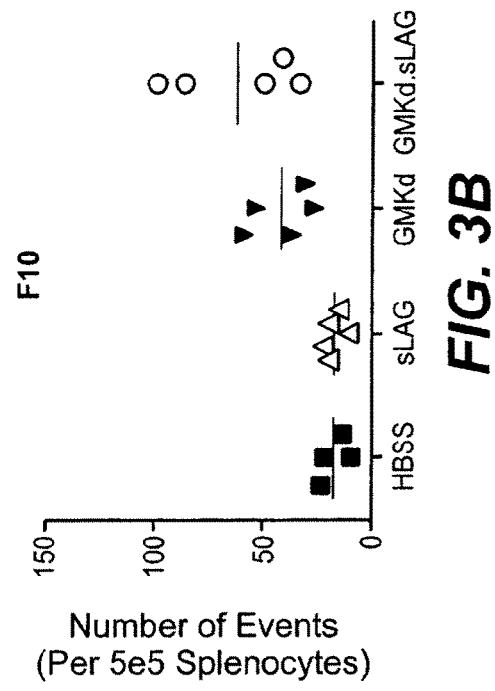
FIG. 3 illustrates the number of antigen-specific T cells reactive against B16 tumor cells following treatment with GM-CSF-secreting tumor cell or LAG-3 or LAG-3 plus GM-CSF-secreting tumor cell combination. On day 0, mice were inoculated SC with live B16 tumor cells. On day 3, mice were immunized with $1 \times 10^6$ irradiated GM-CSF-secreting tumor cells as immunotherapy alone or immunotherapy was followed by daily injections of 0.1 μg of LAG-3 on days 5 to 7 as combination therapy. LAG-3 monotherapy-treated mice were treated on days 5 to 7. On day 10, spleens (n=5) were removed and an ELISPOT was performed to evaluate the number of IFNγ-secreting cells/$5 \times 10^5$ splenocytes when stimulated with irradiated B16F10 cells, trp2 peptide or gp 100 peptide.
Figure 3B:
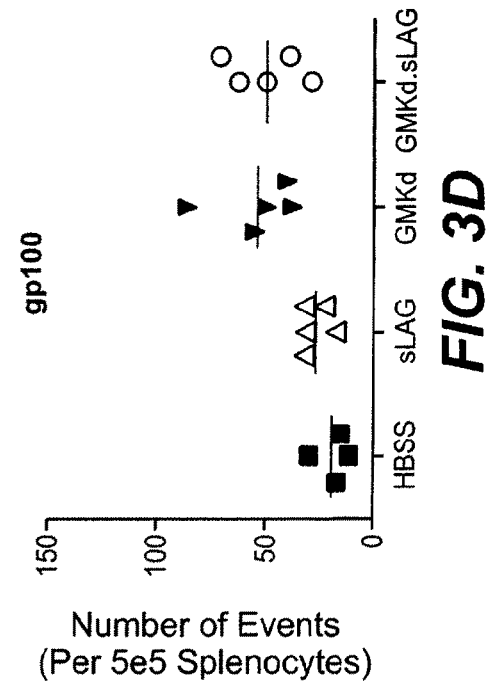
Figure 3C:
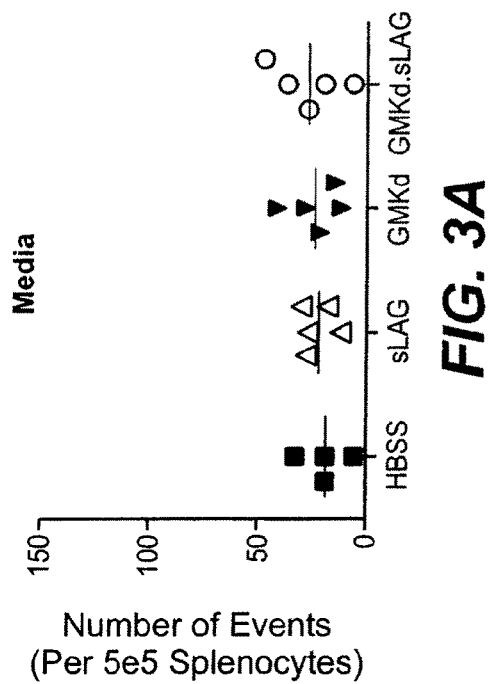
Figure 3D:
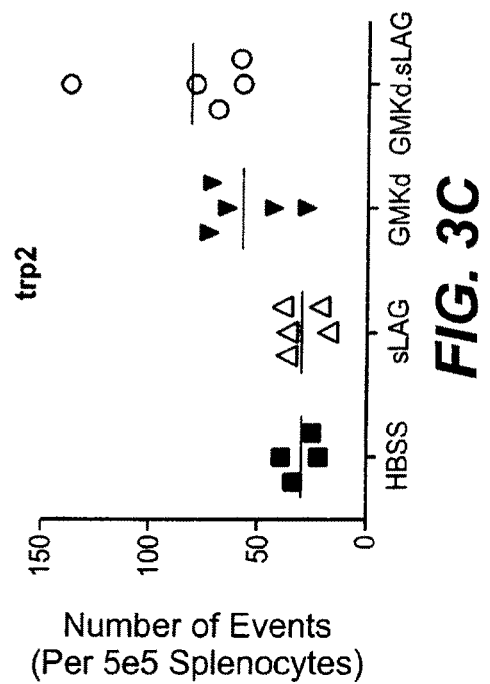

Previous studies have shown that transfection of a gene encoding IL-2 into a tumor cell stimulated an MHC class I-restricted cytolytic T lymphocyte (CTL) response against the tumor in vivo, suggesting that IL-2 can play a role in enhancing the immune responsiveness to a tumor in vivo (Frost et al., WO 92/05262; Fearon et al., Cell 1990 Feb. 9; 60(3):397-403). An exemplary IL-2 sequence for use in practicing the invention may be found for example at GenBank Accession No. NMIL04 and NM_000586, each expressly incorporated by reference herein. Previous studies in the B16 melanoma model have shown that cells expressing both IL-2 and GM-CSF can generate systemic immunity and enhanced survival, as described in International Patent Publication No. WO 00/72686, expressly incorporated by reference herein. Cytolytic activity against B16 tumor cells from animals treated with GM-CSF-secreting tumor cell or LAG-3 or LAG-3 plus GM-CSF-secreting tumor cell combination is shown in FIG. 2. The in vivo CTL results show that treatments with LAG-3 augment the cytolytic activity of splenocytes from mice treated with the combination of LAG-3 plus GM-CSF-secreting tumor cell. Individual kinetics of the entire experiment is shown in FIG. 2.

These results demonstrate that in practicing the present invention an autologous, allogeneic, or bystander cytokine-expressing cellular immunotherapy may be administered to a cancer patient in combination with an antigen presenting cell (APC) activator resulting in enhanced therapeutic efficacy and prolonged survival relative to either monotherapy alone.

In a preferred aspect of the methods described herein, a cytokine-expressing cellular immunotherapy combination is administered to a cancer patient, wherein the cytokine-expressing cellular immunotherapy comprises mammalian, preferably human tumor cells, and the cells in the cytokine-expressing cellular immunotherapy are rendered proliferation incompetent, such as by irradiation. Administration of a cytokine-expressing cellular immunotherapy combination results in an enhanced immune response to the cancer as compared to the immune response to the same cancer following administration of the cytokine-expressing cellular immunotherapy or cancer therapeutic agent or treatment component of the combination alone. In other words, the combined administration of a cytokine-expressing cellular immunotherapy and at least one additional antigen presenting cell (APC) activator or treatment described above results in enhanced therapeutic efficacy as compared to administration of a cytokine-expressing cellular immunotherapy alone or administration of the antigen presenting cell (APC) activator(s) or treatment(s) alone.

The cytokine-expressing cellular immunotherapy combination may be administered by any suitable route. Preferably, the composition is administered subcutaneously or intratumorally. Local or systemic delivery can be accomplished by administration comprising administration of the combination into body cavities, by parenteral introduction, comprising intramuscular, intravenous, intraportal, intrahepatic, peritoneal, subcutaneous, or intradermal administration. In the event that the tumor is in the central nervous system, the composition is administered in the periphery to prime naive T-cells in the draining lymph nodes. The activated tumor-specific T-cells are able to cross the blood/brain barrier to find their targets within the central nervous system.

In one exemplary preferred embodiment, the cytokine-expressing cellular immunotherapy expresses the cytokine, GM-CSF, and the at least one additional antigen presenting cell (APC) activator or treatment is LAG-3.

As will be understood by those of skill in the art, the optimal treatment regimen will vary. As a result, it will be understood that the status of the cancer patient and the general health of the patient prior to, during, and following administration of a cytokine-expressing cellular immunotherapy combination, the patient will be evaluated in order to determine if the dose of each component and relative timing of administration should be optimized to enhance efficacy or additional cycles of administration are indicated. Such evaluation is typically carried out using tests employed by those of skill in the art to evaluate traditional cancer chemotherapy, as further described below in the section entitled "Monitoring Treatment".

Dependent upon the additional antigen presenting cell (APC) activator or treatment, the cytokine-expressing cellular immunotherapy is administered to the patient prior to, at the same time or following the administration of the additional antigen presenting cell (APC) activator or treatment. For example, in the case of an antigen presenting cell (APC) activator, the GM-CSF-expressing cellular immunotherapy is administered to the patient prior to administration of LAG-3. In certain embodiments, the APC activator is administered one, two, three, four, five, six, seven, or more days subsequent to the GM-CSF-expressing cellular immunotherapy. In certain embodiments, the APC activator is administered three days subsequent to the GM-CSF-expressing cellular immunotherapy. In certain embodiments, the APC activator is administered four days subsequent to the GM-CSF-expressing cellular immunotherapy.

Monitoring Treatment

One skilled in the art is aware of means to monitor the therapeutic outcome and/or the systemic immune response upon administering a combination treatment of the present invention. In particular, the therapeutic outcome can be assessed by monitoring attenuation of tumor growth and/or tumor regression and or the level of tumor specific markers. The attenuation of tumor growth or tumor regression in response to treatment can be monitored using one or more of several end-points known to those skilled in the art including, for instance, number of tumors, tumor mass or size, or reduction/prevention of metastasis.

All literature and patent references cited herein are hereby expressly incorporated by reference herein.

EXAMPLE 1

Cytokine-Expressing Cellular Immunotherapies Plus LAG-3

In vivo studies were carried out using the B16F10 model to determine if a LAG-3 in combination with a cytokine-expressing cellular immunotherapy can enhance anti-cancer efficacy. The optimal timing of LAG-3 administration relative to GM-CSF-expressing cellular immunotherapy is determined. For these experiments, a soluble form of the murine LAG-3 protein, mLAG-3Ig, was used. This molecule, mLAG-3Ig is described, for example, in El Mir & Triebel, 2000, *J. Immunol.* 164: 5583-9.

On day 0 mice were challenged with $2 \times 10^5$ live B16F10 (by SC injection at a dorsal site in 0.5 ml volume). On day 3, mice were vaccinated with $1 \times 10^6$ irradiated immunotherapy cells (as indicated in Tables 1 and 2, below), followed by injection of LAG-3. A combination of GM-CSF-secreting tumor cell immunotherapy and LAG-3 were administered at Day 3, 4, 7, and 11.

Mice were assessed daily for any obvious abnormality and if subcutaneous tumors reached 15-20 mm-diameter in size or started to ulcerate through the skin animals were euthanized. On day 21, spleens and blood were collected and used for analysis of anti-tumor CTL, cytokine release (ELISA) and intracellular FACS.

TABLE 1

| Animal ID | n | Tumor Challenge (D0) | Tumor Vaccine (D3) | sLAG3 (0.1 µg/injection) |
|---|---|---|---|---|
| 100 A-J | 10 | 2 × 10e5 B16F10 | HBSS | NA |
| 200 A-J | 10 | 2 × 10e5 B16F10 | 1 × 10e6 B16.GM kd | NA |
| 300 A-J | 10 | 2 × 10e5 B16F10 | HBSS | D3 |
| 400 A-J | 10 | 2 × 10e5 B16F10 | 1 × 10e6 B16.GM kd | Day 3 (10/2) |
| 500 A-J | 10 | 2 × 10e5 B16F10 | 1 × 10e6 B16.GM kd | Day 4 (10/3) |
| 600 A-J | 10 | 2 × 10e5 B16F10 | 1 × 10e6 B16.GM kd | Day 7 (10/6) |
| 700 A-J | 10 | 2 × 10e5 B16F10 | 1 × 10e6 B16.GM kd | Day 11 (10/10) |

The results indicate that the combined administration of GM-CSF-secreting tumor cell immunotherapy and LAG-3 enhanced percent survival (FIGS. 1A-1D) relative to administration of GM-CSF-secreting tumor cell immunotherapy alone, for up to 49 days post-challenge.

A further suggestion as to the potential utility if the combination of GM-CSF-secreting immunotherapies and LAG-3 in eliciting an anti-tumor immune response is the production of effector cytokines such as TNF-alpha, IL-2, and IFN-gamma upon restimulation in vitro. Release of such cytokines is often used as a surrogate marker for monitoring tumor-specific immune responses following immunotherapeutic strategies designed to induce anti-tumor immunity. When cytokine levels were measured in supernatants from spleen cells restimulated in vitro for 48 hours with irradiated GM-CSF-secreting tumor cells the production of TNF-alpha, IL-5 and IL-2 was detected by week two (data not shown). The results for the production of INF-gamma secreting cells per $5 \times 10^5$ splenocytes when stimulated with irradiated B16F10 cells, Trp2 peptide or gp100 peptide are shown in FIG. 3.

Immune Response Following Repeated Treatment with a GM-CSF-Secreting Immunotherapy Combined with Treatment with LAG-3

Immune responses were measured as increases in tumor antigen-specific T-cells. Such T-cells can be identified by the induction of intracellular IFN-gamma expression following stimulation with a tumor-specific peptide bound to MHC I. A prostate tumor-specific antigen that is both a murine prostate adenocarcinoma cell-specific epitope and shared with human prostate cancer. Intracellular cytokine staining (ICS) may be used to monitor tumor-specific T-cell responses and to identify very low frequencies of antigen-specific T-cells. Because ICS is performed on freshly isolated lymphocytes within 5 hours of removal, unlike the cytolytic assay, which often requires 5-7 days of in vitro stimulation, it can be used to estimate the frequency of tumor antigen-specific T-cells in vivo. This provides a means to compare the potency of different tumor immunotherapy strategies. In this study, ICS was utilized to monitor T-cell responses to the prostate tumor-specific antigen described above after treatment with the murine prostate adenocarcinoma cell-GM immunotherapy with and without LAG-3 co-treatment. In one embodiment, the number of antigen-specific T cells in B16 tumor cells treated with GM-C SF-secreting tumor cell or LAG-3 or LAG-3 plus GM-CSF-secreting tumor cell combination was determined. On day 0, mice were inoculated SC with live B16 tumor cells. On day 3, mice were immunized with 1×10⁶ irradiated GM-CSF-secreting tumor cells as immunotherapy alone or immunotherapy was followed by daily injections of LAG-3 on days 5 to 7 as combination therapy. LAG-3 mono-therapy-treated mice were treated on days 5 to 7. On day 10, spleens (n=5) were removed and an ELISPOT was performed to evaluate the number of IFNγ-secreting cells/5×10⁵ splenocytes when stimulated with irradiated B16F10 cells, trp2 peptide or gp100 peptide. The results are shown in FIG. 3. Sharp increases in the number of antigen-specific T cells were detected in mice treated with irradiated B16F10 cells, Trp2 peptide or gp100 peptide.

Figure 5A:
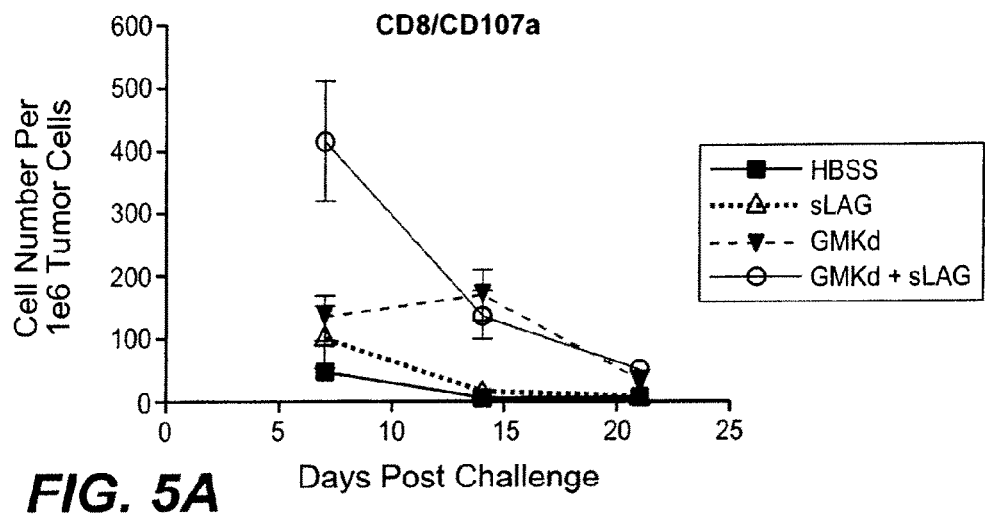
FIG. 5A illustrates T cells double positive for CD8/CD107a/$1 \times 10^6$ tumor cells following treatment with GM-CSF-secreting tumor cell or LAG-3 or LAG-3 plus GM-CSF-secreting tumor cell combination. On day 0, mice were inoculated SC with live B16 tumor cells. On day 3, mice were immunized with $1 \times 10^6$ irradiated GM-CSF-secreting tumor cells as immunotherapy alone or immunotherapy was followed by daily injections of 0.1 μg of LAG-3 on days 5 to 7 as combination therapy. LAG-3 monotherapy-treated mice were treated on days 5 to 7. At indicated timepoints, tumors (n=5) were removed, digested, stained and evaluated by flow cytometry.
Figure 5B:
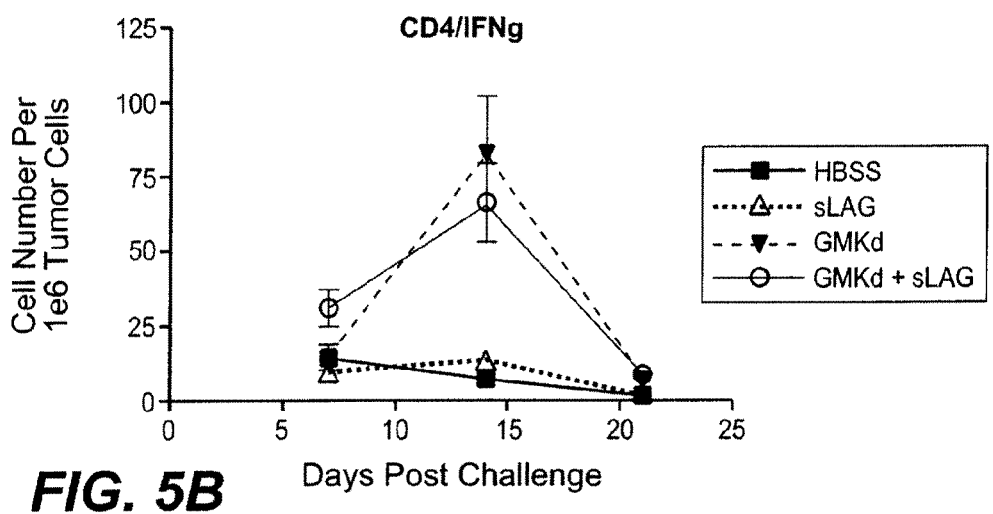
FIG. 5B illustrates T cells double positive for CD4/IFNγ/$1 \times 10^6$ tumor cells following treatment with GM-CSF-secreting tumor cell or LAG-3 or LAG-3 plus GM-CSF-secreting tumor cell combination. On day 0, mice were inoculated SC with live B16 tumor cells. On day 3, mice were immunized with $1 \times 10^6$ irradiated GM-CSF-secreting tumor cells as immunotherapy alone or immunotherapy was followed by daily injections of 0.1 μg of LAG-3 on days 5 to 7 as combination therapy. LAG-3 monotherapy-treated mice were treated on days 5 to 7. At indicated timepoints, tumors (n=5) were removed, digested, stained and evaluated by flow cytometry.
Figure 5C:
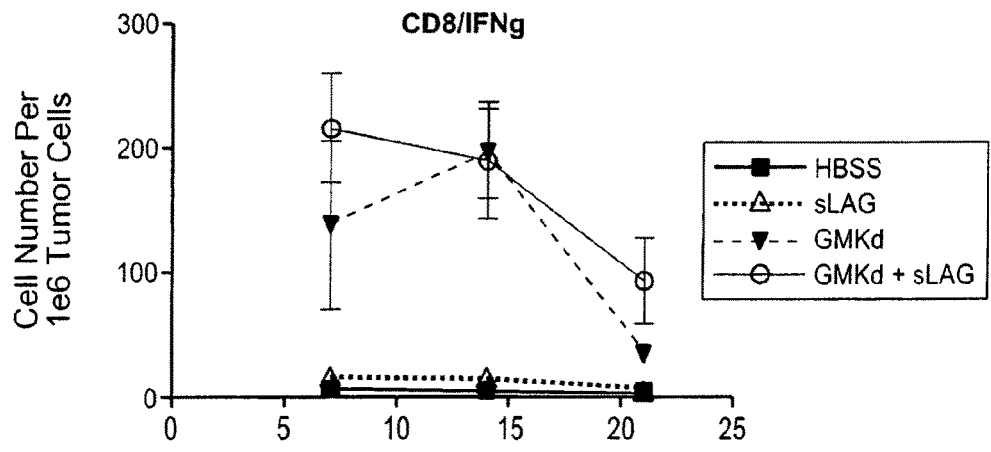
FIG. 5C illustrates T cells double positive for CD8/IFNγ/$1 \times 10^6$ tumor cells following treatment with GM-CSF-secreting tumor cell or LAG-3 or LAG-3 plus GM-CSF-secreting tumor cell combination. On day 0, mice were inoculated SC with live B16 tumor cells. On day 3, mice were immunized with $1\times10^6$ irradiated GM-CSF-secreting tumor cells as immunotherapy alone or immunotherapy was followed by daily injections of 0.1 µg of LAG-3 on days 5 to 7 as combination therapy. LAG-3 monotherapy-treated mice were treated on days 5 to 7. At indicated timepoints, tumors (n=5) were removed, digested, stained and evaluated by flow cytometry.
Figure 6A:
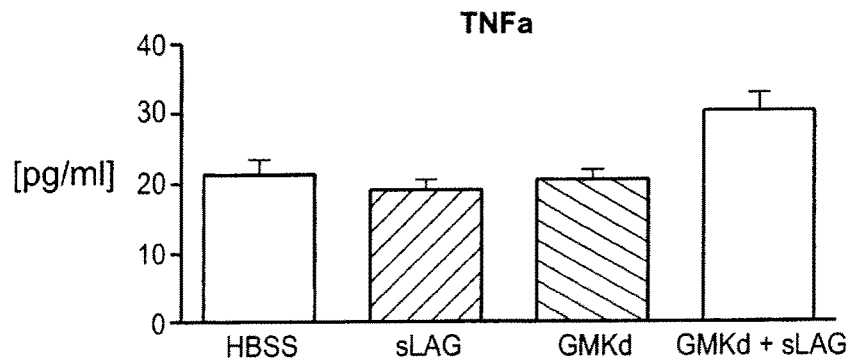
FIGS. 6A-6F illustrate pro-inflammatory, Th1, and Th2 cytokine secretion by splenocytes from animals treated with GM-CSF-secreting tumor cell immunotherapy and LAG3. Tumor-bearing mice (n=5 per group; tumors were induced with B16 vells) were immunized with $1\times10^6$ irradiated GM-CSF-secreting tumor cells 3 days post tumor inoculation. LAG-3 (0.1 µg) was given on days 5-7 post tumor inoculation as a monotherapy and to mice administered the GM-CSF-secreting tumor cells as a combination therapy. On day 10, supernatant from splenocytes co-cultured with irradiated B16F10 cells for 2 days were evaluated using Th1/Th2 and inflammatory cytometric bead array kits by flow cytometry. Cytokine secretion levels are shown for TNFa (FIG. 6A), IFNγ(FIG. 6B), IL-5 (FIG. 6C), IL-6 (FIG. 6D), IL-10 (FIG. 6E), and MCP-1 (FIG. 6F).
Figure 6B:
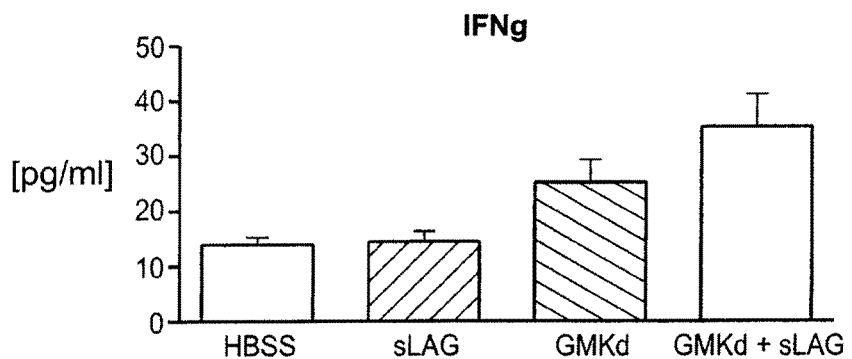
Figure 6C:
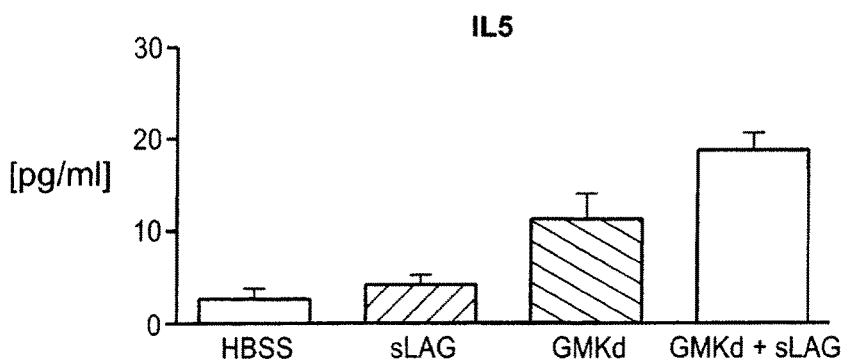
Figure 6D:
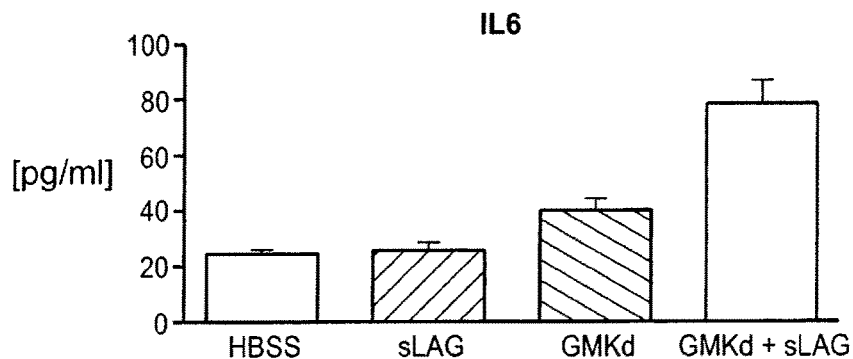
Figure 6E:
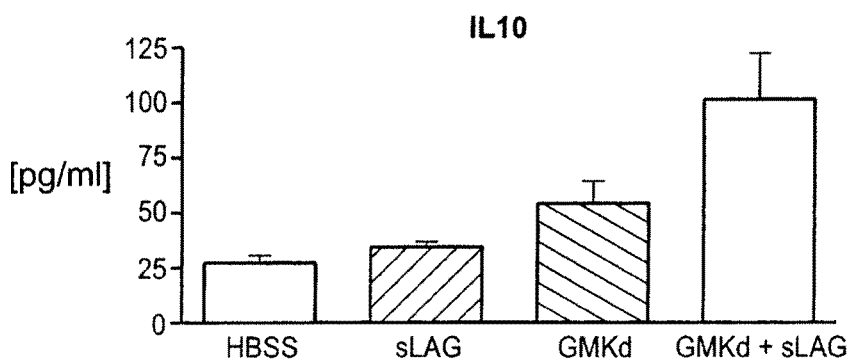
Figure 6F:
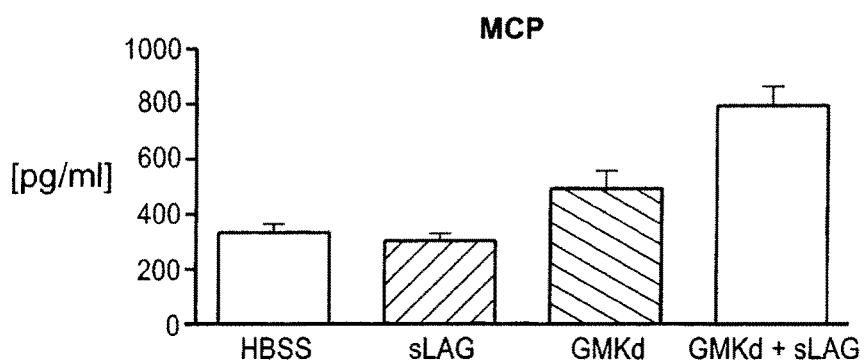
Figure 7A:
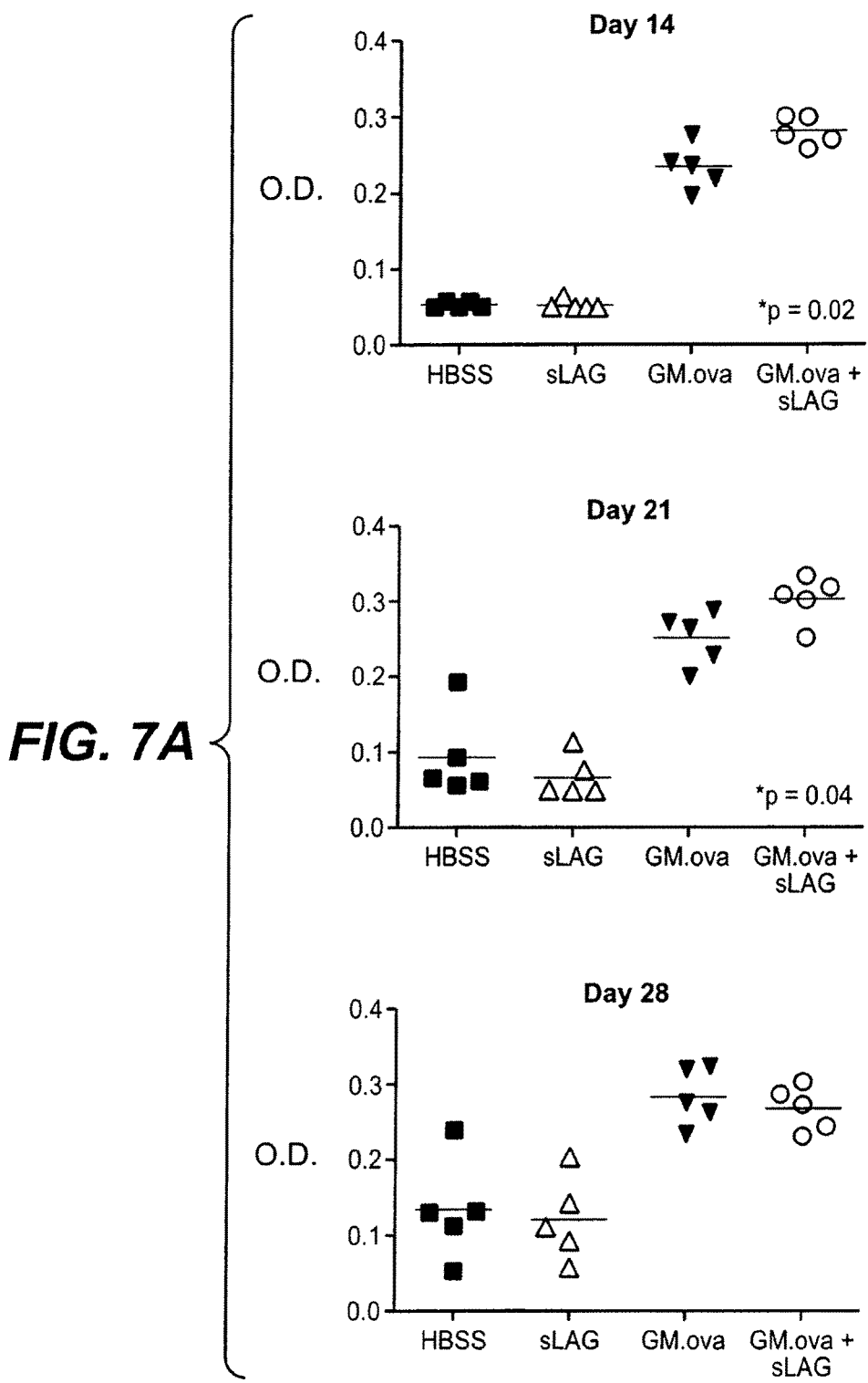
FIGS. 7A and 7B illustrate effects of LAG-3 on antigen-specific IgG1 and antigen-specific IgG2a levels of GM-CSF-secreting tumor cell immunotherapy-treated animals. Tumor-bearing mice (n=5 per group; mice were inoculated SC with live B16 tumor cells transduced to express the surrogate antigen ovalbumin). were immunized with $1\times10^6$ irradiated GM.ova cells 3 days post tumor inoculation. LAG-3 (0.1 µg)] was given on days 5-7 post tumor inoculation as monotherapy and to GM.ova-treated mice as combination therapy. At indicated timepoints, serum samples were acquired for antigen-specific humoral responses by anti-ovalbumin ELISA. Shown are the kinetics data for the isotypes of (A) IgG1 performed at serum dilutions of 1:500 and (B) IgG2a performed at serum dilutions of 1:50.
Figure 7B:
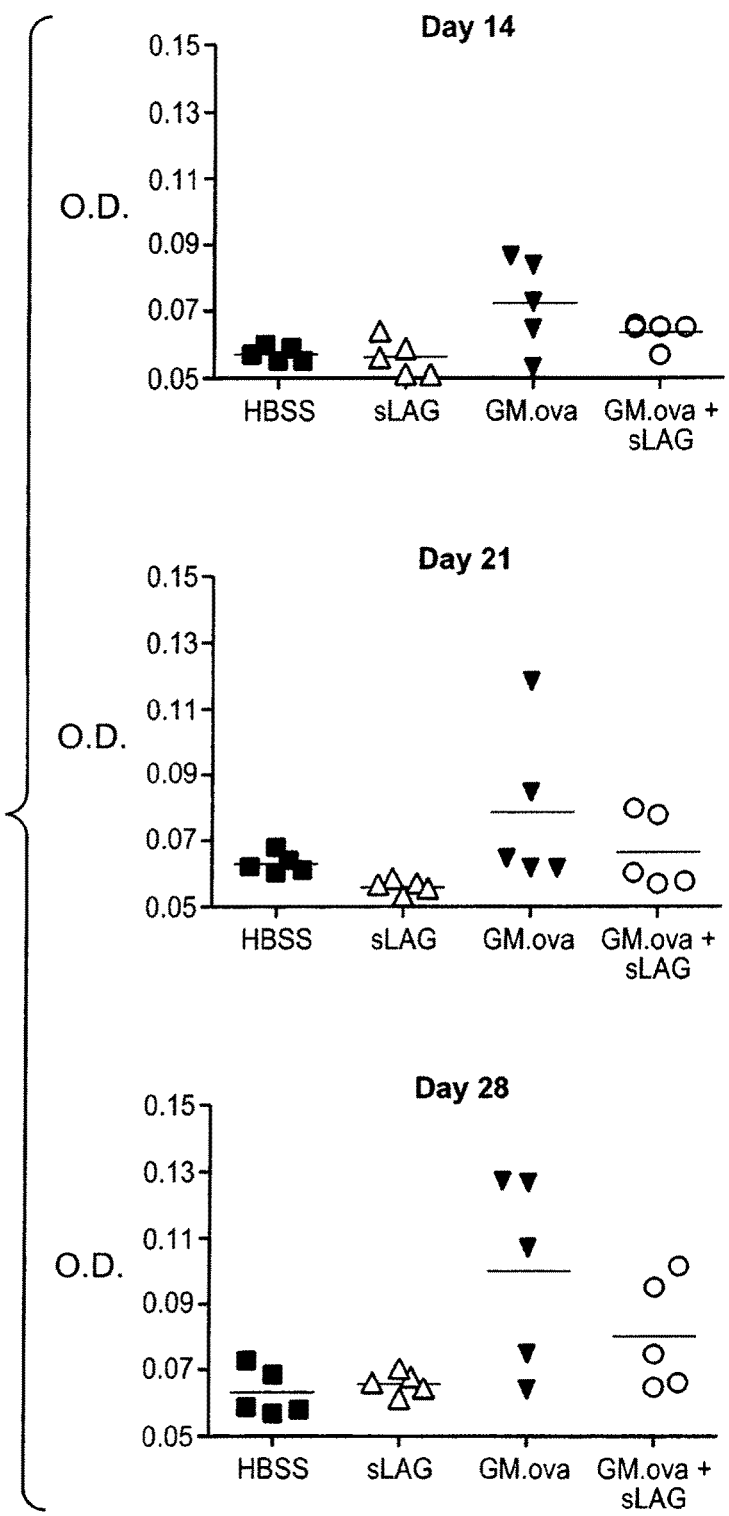

In another embodiment, rapid effector T cells infiltration into B16 tumor cells was detected in mice treated with GM-CSF-secreting tumor cells and LAG-3 (FIGS. 5A-5C). Double positive T cells per 1×10⁶ B16 tumor cells for CD8/CD107a, CD4/INFγ, and CD8/INFγ are shown in FIGS. 5A, 5B and 5C, respectively.

EXAMPLE 2

Assay for Identifying a LAG-3 Protein that can Activate an Antigen Presenting Cell The following example provides an exemplary protocol that can be used to determine whether a LAG-3 protein activates an antigen presenting cell. Briefly, the protocol includes incubating suitable antigen presenting cells with increasing concentrations of a LAG-3 protein, then detecting whether and how much cytokines are released by the antigen presenting cells in response to LAG-3 protein binding. If 0.1 to 1 µg LAG-3 protein can induce the antigen presenting cells to release more than 1 ng/ml of cytokine above background the LAG-3 protein is capable of activating the antigen presenting cell.

In the assay, 0.2×10⁶ peripheral blood mononuclear cells (PMBCs) in 100 µl synthetic culture medium (X-VIVO10, Lonza Ltd) without serum are aliquoted to individual wells of a microtiter dish. LAG-3 protein to be assayed is added to a first well at a final concentration of 4000 ng/ml, then serially diluted by 2 to achieve final concentrations of 2000, 1000, 500, 250, 125, and 62.5 ng/ml, respectively. The plate is then incubated at 37° C. for 24 hours.

Next, the concentration of a cytokine released by the PBMCs in response to LAG-3 protein binding is assessed. In this example, the concentration of CCL4/MIP-1β is assessed using a BD™ Cytometric Bead Array according to the manufacturer's instructions. A standard ELISA can also be used to detect and/or quantify cytokine production.

Figure 8:
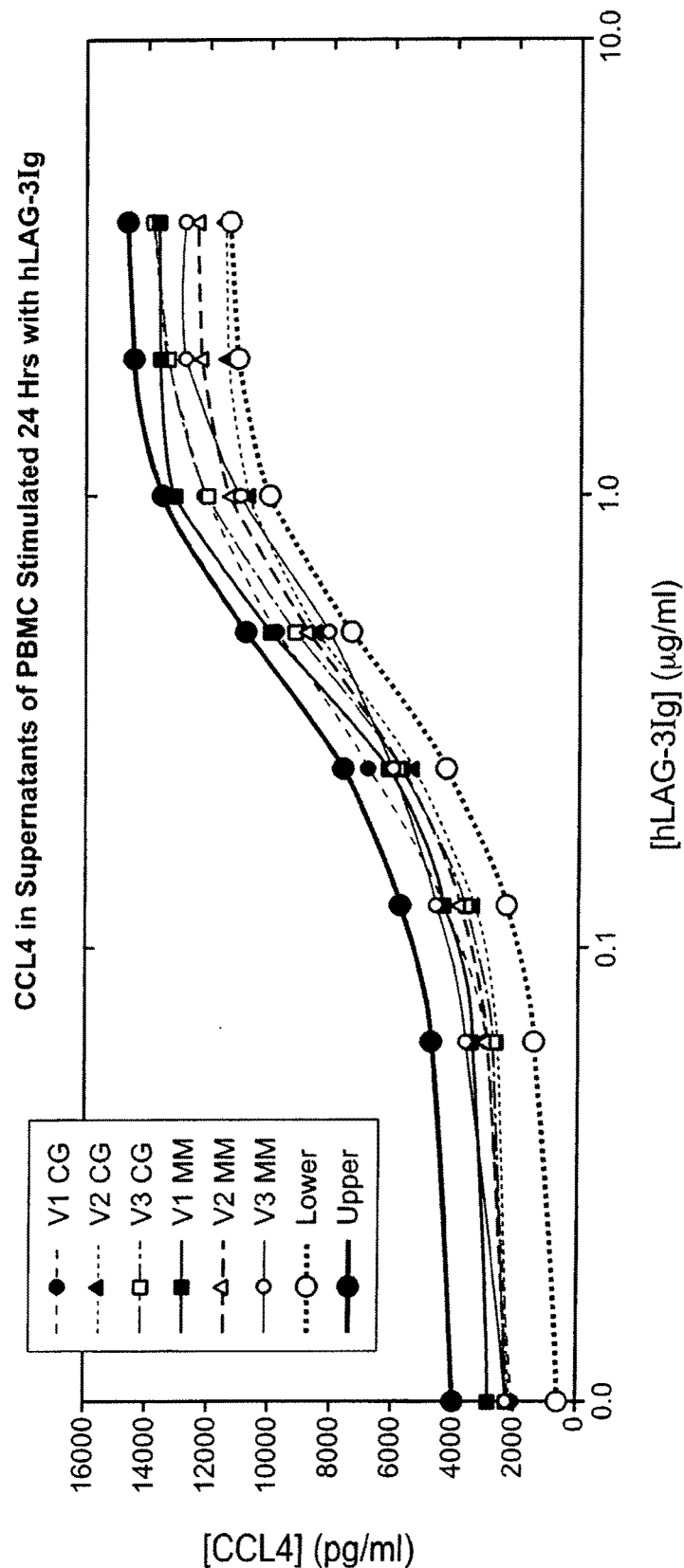
FIG. 8 presents a representative curve showing concentrations of CCL4 released following stimulation for 24 hours with varying concentrations of a representative LAG-3 protein that can activate an antigen presenting cell in accordance with the present invention.

A LAG-3 protein that activates an antigen presenting cell according to the present invention induces at least about 4 ng/ml CCL4 above background at about 0.5 µg/ml LAG-3 protein in the assay as described above. FIG. 8 presents a representative curve showing concentrations of CCL4 released following stimulation for 24 hours with varying concentrations of a representative LAG-3 protein.

TABLE 2

| Animal ID | n | Tumor Challenge (D0) | Tumor Vaccine (D3) | sLAG3 |
|---|---|---|---|---|
| 100 A-J | 10 | 2 × 10e5 B16F10 | HBSS | NA |
| 200 A-J | 10 | 2 × 10e5 B16F10 | 1 × 10e6 B16.GM kd | NA |
| 300 A-J | 10 | 2 × 10e5 B16F10 | HBSS | 1 µg/injection (D4) |
| 400 A-J | 10 | 2 × 10e5 B16F10 | 1 × 10e6 B16.GM kd | 1 µg/injection (D4) |
| 500 A-J | 10 | 2 × 10e5 B16F10 | 1 × 10e6 B16.GM kd | 0.1 µg/injection (D4) |
| 600 A-J | 10 | 2 × 10e5 B16F10 | 1 × 10e6 B16.GM kd | 0.01 µg/injection (D4) |
| 700 A-J | 10 | 2 × 10e5 B16F10 | 1 × 10e6 B16.GM kd | 0.1 µg/injection (D5) |
| 800 A-J | 10 | 2 × 10e5 B16F10 | 1 × 10e6 B16.GM kd | 0.1 µg/injection (D6) |
| 900 A-J | 10 | 2 × 10e5 B16F10 | 1 × 10e6 B16.GM kd | 0.1 µg/injection (D7) |

SEQ ID NO.: 1 - Human LAG-3 protein
LQPGAEVPVVWAQEGAPAQLPCSPTIPLQDLSLLRRAGVTWQHQPDSGPP

AAAPGHPLAPGPHPAAPSSWGPRPRRYTVLSVGPGGLRSGRLPLQPRVQL

DERGRQRGDFSLWLRPARRADAGEYRAAVHLRDRALSCRLRLRLGQASMT

ASPPGSLRASDWVILNCSFSRPDRPASVHWFRNRGQGRVPVRESPHHHLA

ESFLFLPQVSPMDSGPWGCILTYRDGFNVSIMYNLTVLGLEPPTPLTVYA

GAGSRVGLPCRLPAGVGTRSFLTAKWTPPGGGPDLLVTGDNGDFTLRLED

VSQAQAGTYTCHIHLQEQQLNATVTLAIITVTPKSFGSPGSLGKLLCEVT

PVSGQERFVWSSLDTPSQRSFSGPWLEAQEAQLLSQPWQCQLYQGERLLG

AAVYFTELSSPGAQRSGRAPGALPAGHLLLFLTLGVLSLLLLVTGAFGFH

LWRRQWRPRRFSALEQGIHPPQAQSKIEELEQEPEPEPEPEPEPEPEPEP

EQL

SEQ ID NO.: 2 - a soluble form of the LAG-3 protein (hLAG-3Ig)
LQPGAEVPVVWAQEGAPAQLPCSPTIPLQDLSLLRRAGVTWQHQPDSGPP

AAAPGHPLAPGPHPAAPSSWGPRPRRYTVLSVGPGGLRSGRLPLQPRVQL

DERGRQRGDFSLWLRPARRADAGEYRAAVHLRDRALSCRLRLRLGQASMT

ASPPGSLRASDWVILNCSFSRPDRPASVHWFRNRGQGRVPVRESPHHHLA

ESFLFLPQVSPMDSGPWGCILTYRDGFNVSIMYNLTVLGLEPPTPLTVYA

GAGSRVGLPCRLPAGVGTRSFLTAKWTPPGGGPDLLVTGDNGDFTLRLED

VSQAQAGTYTCHIHLQEQQLNATVTLAIITVTPKSFCSPGSLGKLLCEVT

PVSGQERFVWSSLDTPSQRSFSGPWLEAQEAQLLSQPWQCQLYQGERLLG

AAVYFTELSSPGDDDDKGSGSGEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKT

TPPVLDSDGSFSLYSKLTVDKSRWQQGNVFSCSVMHEALHNHYTQKSLSL

SPGK

The linker peptide between the hLAG3 P4 domain and the hinge region of a hinge -CH2-CH3 hIgG1 Fc region is shown in bold.

What is claimed is:

1. A composition for stimulating an immune response to cancer in a subject, comprising a synergistic combination of:
   a) an allogeneic tumor cell line comprising cells that express an antigen of the cancer and that express GM-CSF and which cells have been rendered proliferation-incompetent and
   b) an APC activator which is LAG-3.

2. The composition of claim 1, wherein the cells of said cell line are rendered proliferation-incompetent by irradiation.

3. The composition of claim 1, wherein said allogeneic cell line is a tumor cell line selected from the group consisting of a prostate tumor line, a non-small cell lung carcinoma line and a pancreatic cancer line.

4. The composition of claim 1, wherein said LAG-3 is expressed by cells autologous to said subject, or allogeneic to said subject, or are bystander cells.

5. The composition of claim 4, wherein the cells that express LAG-3 are rendered proliferation-incompetent by irradiation.

6. A method for stimulating an immune response to cancer in a subject which comprises administering to a subject in need of such stimulating an effective amount of the composition of claim 1.

* * * * *